United States Patent
DeLisa et al.

(10) Patent No.: US 9,150,850 B2
(45) Date of Patent: Oct. 6, 2015

(54) COMPOSITIONS AND METHODS FOR ANALYZING PROTEIN INTERACTIONS

(75) Inventors: Matthew DeLisa, Ithaca, NY (US); George Georgiou, Austin, TX (US); Dujduan Waraho, Ithaca, NY (US)

(73) Assignees: CORNELL RESEARCH FOUNDATION, INC., Ithaca, NY (US); RESEARCH DEVELOPMENT FOUNDATION, Carson City, NV (US)

( * ) Notice: Subject to any disclaimer, the term of this patent is extended or adjusted under 35 U.S.C. 154(b) by 859 days.

(21) Appl. No.: 12/064,292

(22) PCT Filed: Aug. 22, 2006

(86) PCT No.: PCT/US2006/032810
§ 371 (c)(1),
(2), (4) Date: Oct. 2, 2008

(87) PCT Pub. No.: WO2007/024877
PCT Pub. Date: Mar. 1, 2007

(65) Prior Publication Data
US 2009/0220952 A1 Sep. 3, 2009

Related U.S. Application Data

(60) Provisional application No. 60/710,597, filed on Aug. 22, 2005.

(51) Int. Cl.
*C40B 30/04* (2006.01)
*C12N 15/10* (2006.01)
*G01N 33/50* (2006.01)

(52) U.S. Cl.
CPC ........ *C12N 15/1055* (2013.01); *G01N 33/5032* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 5,935,824 A | 8/1999 | Sgarlato | |
| 5,990,275 A | 11/1999 | Whitlow et al. | |
| 6,867,042 B2 | 3/2005 | Waldo | |
| 6,936,421 B2 * | 8/2005 | Anderson et al. | 506/10 |
| 7,252,952 B2 * | 8/2007 | Lorens et al. | 435/7.1 |
| 2002/0110860 A1 | 8/2002 | Bron et al. | |
| 2003/0064435 A1 | 4/2003 | Weiner | |

(Continued)

FOREIGN PATENT DOCUMENTS

| | | |
|---|---|---|
| WO | 9222657 | 12/1992 |
| WO | 03083056 | 10/2003 |
| WO | 2004050871 | 6/2004 |

OTHER PUBLICATIONS

Cattaneo (TIBTECH, 1999 (vol. 17), pp. 115-120).*

(Continued)

*Primary Examiner* — Christian Boesen
(74) *Attorney, Agent, or Firm* — Casimir Jones, S.C.

(57) ABSTRACT

The present invention relates to compositions and methods for analyzing and modulating (e.g., enhancing or inhibiting) protein-protein interactions. In particular, compositions and methods of the present invention find use in identifying, reconstituting and characterizing protein-protein interactions, identifying binding subunits, and drug screening. The methods and compositions of the invention may also be used to identify agents that may agonize or antagonize a protein-protein interaction (e.g., using test compounds).

13 Claims, 4 Drawing Sheets

(56) References Cited

U.S. PATENT DOCUMENTS

| | | | |
|---|---|---|---|
| 2003/0096306 A1* | 5/2003 | Maur et al. | 435/7.1 |
| 2003/0180937 A1 | 9/2003 | Georgiou | |
| 2003/0219870 A1 | 11/2003 | Georgiou | |
| 2004/0077090 A1 | 4/2004 | Short | |
| 2005/0124010 A1 | 6/2005 | Short et al. | |
| 2005/0182138 A1 | 8/2005 | John et al. | |
| 2006/0078875 A1* | 4/2006 | Benkovic et al. | 435/4 |
| 2007/0026012 A1* | 2/2007 | DeLisa et al. | 424/190.1 |
| 2008/0287315 A1 | 11/2008 | Delisa | |
| 2009/0298089 A1* | 12/2009 | Rossner et al. | 435/7.1 |
| 2010/0144546 A1 | 6/2010 | Delisa et al. | |

OTHER PUBLICATIONS

Collard (Belgian Biosafety Server, http://www.antibioresistance.be/betalactamases.html (1999).
Seehaus et al, Gene, 114: 235-237 (1992).
Georgiou and Valax, "Expression of correctly folded proteins in *Escherichia coli*" Curr Opinion Biotechnolol 7, 190-197 (1996).
Maxwell et al, "A simple in vivo assay for increased protein solubility," Protein Sci 8, 1908-1911 (1999).
Waldo et al, "Rapid protein-folding assay using green fluorescent protein," Nat Biotechnolol 17, 691-695 (1999).
Cabantous et al, "Protein tagging and detection with engineered self-assembling fragments of green fluorescent protein," Nat Biotechnol 23, 102-107 (2005).
Wigley et al, "Protein solubility and folding Illonitored in vivo by structural cOlllplelllentation of a genetic Illarker protein," Nat Biotechnol 19, 131-136 (2001).
Lesley et al, Protein Eng 15, 153-160 (2002).
Tsumoto et al, "Solubilization of active green fluorescent protein from insoluble particles by guanidine and arginine," Biochem Biophys Res Commun 312, 1383-1386 (2003).
Roodveldt et al, Curr Opinion Struct Biol 15, 50-56 (2005).
Wall et al "Effects of overexpressing folding modulators on the in vivo folding of. heterologous proteins in *Escherichia coli* ," Curr Opin Biotechnol 6, 507-516 (1995).
Berks, "A common export pathway for proteins binding complex redox cofactors?," Mol Microbiol 22, 393-404 (1996).
Settles et al, "Sec-Independent Protein Translocation by the Maize Hcf106 Protein," Science 278, 1467-1470 (1997).
Weiner et al, "A Novel and Ubiquitous System for Membrane Targeting and Secretion of Cofactor-Containing Proteins," Cell 93, 93-101 (1998).
Sanders et al, "Transport of cytochrome c derivatives by the bacterial Tat protein translocation system" Mol Microbiol 41, 241-246 (2001).
Lutz et al, "A universal, vector-based system for nucleic acid reading-frame Selection," Protein Eng 15, 1025-1030 (2002).
Delisa et al "Folding quality control in the export of proteins by the bacterial twin-arginine translocation pathway," Proc Natl Acad Sci USA 100, 6115-6120 (2003).
Delisa et al, "Genetic Analysis of the Twin Arginine Translocator Secretion Pathway in Bacteria," J Biol Chem 277, 29825-29831 (2002).
Niviere et al, J Gen Microbiol, 138: 2173-2183 (1992).
Smith et al, J Bacteriol, 169: 3321-3328 (1987).
Delisa et al, "Genetic screen for directed evolution of soluble proteins in bacteria" Abstracts of Papers American Chemical Society, vol. 229 (Mar. 2005) p. U243.
Delisa et al, "Molecular engineering of soluble proteins directly living cells" Abstracts of Papers American Chemical Society, vol. 227, Mar. 2004, pp. U208-U209.
Fisher et al, "Reprogramming the bacterial Tat system for monitoring protein folding directly in cells" AICHE Annual Meeting, Conference, Proceedings, pp. 8751 (2004).
Fisher et al, "Genetic selection for protein solubility enabled by the folding quality control feature of the twin-arginine translocation pathway" Protein Science, vol. 15, Mar. 2006 pp. 449-458.

Arie et al., 2001, "Chaperone function of FkpA, a heat shock prolyl isomerase, in the periplasm of *Escherichia coli*", Mol Microbiol, 39: 199-210.
Bothmann and Pluckthun, 1998, "Selection for a periplasmic factor improving phage display and functional periplasmic expression", Nat Biotechnol, 16: 376-380.
Bowden et al., 1991, "Structure and morphology of protein inclusion bodies in *Escherichia coli*", Biotechnology (N Y), 9: 725-730.
Broome-Smith, 1990, "Beta-lactamase as a probe of membrane portien assembly and protein export", Molecular Microbiology, 4: 1637-1644.
DeLisa et al., 2002, Genetic analysis of the twin arginine translocator secretion pathway in bacteria, J Biol Chem, 277: 29825-29831.
Dyson et al., 2004, "Production of soluble mammalian proteins in *Escherichia coli*: identification of protein features that correslate with successful expression", BMC Biotechnol 4, 32.
Feilmeier et al., 2000, "Green fluorescent protein functions as a reporter for protein localization in *Escherichia coli*", J Bacteriol, 182: 4068-4076.
Fisher et al, 2006, "Genetic selection for protein solubility enabled by the folding quality control feature of the twin-arginine translocation pathway", Protein Science, 15: 449-458.
Frech et al., 1996, "Competition between DsbA-mediated oxidation and conformational folding of RTEM1 beta-lactamase", Biochemistry, 35: 11386-11395.
Missiakas et al., 1996, "New components of protein folding in extracytoplasmic compartments of *Escherichia coli* SurA, FkpA and Skp/OmpH", Mol Micorbiol, 21: 871-884.
Schierle, 2003, "The DsbA Signal Sequence Directs Efficient, Cotranslational Export of Passanger Proteins to the *Escherichia coli* Periplasm via the Signal Recognition Particle Pathway", J Bacteriol., 185: 5706-5713.
Sone et al., 1997, Roles of disulfide bonds in bacterial alkaline phosphatase, J Biol Chem, 272: 6174-6178.
Steiner et al., 2006, "Signal sequences directing cotranslational translocation expand the range of proteins amenable to phage display", Nat Biotechnol, 24: 823-831.
Tomoyasu et al., 2001, "Genetic dissection of the roles of chaperones and proteases in protein folding degradation in the *Escherichia coli* cytosol", Mol Microbiol, 40: 397-413.
Villaverde and Carrio, 2003, "Protein aggregation in recombinant bacteria: biological role of inclusion bodies", Biotechnol Lett, 25: 1385-1395.
International Search Report for Application No: PCT/US06/29998; Dated Aug. 1, 2008.
European Search Report for Application No. EP06/789138; Dated Apr. 21, 2009.
Examiner's Report for Application No. 2006275415; Dated Oct. 29, 2009.
International Search Report for Application No. PCT/US08/50991; Dated Aug. 12, 2008.
Gerth, M.L., et al, "A second-generation system for unbiased reading frame selection," Protein Engineering, Design & Selection, vol. 17, No. 7, pp. 595-602 (2004).
Lutz, S., et al., "A Universal, Vector-Based System for Nucleic Acid Reading-Frame Selection," Protein Engineering, vol. 15, No. 12, pp. 1025-1030 (2002).
Wurth, C., et al., "Mutations that Reduce Aggregation of the Alzheimer's Aβ42 Peptide: an Unbiased Search for the Sequence Determinants of Aβ Amyloidogenesis," J. Mol. Biol. (2002) 319, pp. 1279-1290.
Choi, J.H., and Lee, S.Y., "Secretory and Extracellular Production of Recombinant Proteins Using *Escherichia coli*," App. Microbiol. (2004) 64: pp. 625-635.
Shih, Yan-Ping, "High-Throughput Screening of Soluble Recombinant Proteins," Protein Science (2002), 11: pp. 1714-1719.
Philibert Pascal et al, "Directed evolution of single-chain Fv for cytoplasmic expression using the [beta]-galactosidase complementation assay results in proteins highly susceptible to protease degradation and aggregation," Microbial Cell Factories, Biomed Central, London, NL, vol. 3, No. 1, Dec. 17, 2004, p. 16.
Brondijk, et al., "NapGH components of the periplasmic nitrate reductase of *Escherichia coli* K-12: location, topology and physi-

(56) References Cited

OTHER PUBLICATIONS ological roles in quinol oxidation and redox balancing", Biochemical Journal, vol. 379, No. Part 1, Apr. 1, 2004, pp. 47-55, XP002496811.
Department of Biomedical Engineering: "2004-2005 Annual Report" [Online]—2005, pp. 1-60, XP002496810 The University of Texas at Austin, Retrieved from the Internet: URL: http://www.bme.utexas.edu/pdf/BME%20Annual%20Report%202004-2005.pdf> [retrieved on Sep. 23, 2008].
Dubini et al, "Assembly of Tat-dependent [NiFe] hydrogenases: identification of precursor-binding accessory proteins", FEBS Letters, Elsevier, Amsterdam, NL, vol. 549, No. 1-3, Aug. 14, 2003, pp. 141-146, XP004446879.
European Search Report for Application No. EP06/789929; Dated Sep. 23, 2008.
International Search Report for Application No. PCT/US06/32810; Dated Mar. 6, 2007.
Strauch et al: "Towards functional genomics: A novel two-hybrid system using the TAT machinery", American Chemical Society. Abstracts of Paper. At the National Meeting, American Chemical Society, Washington DC, US, vol. 229, No. Part 1, Mar. 17, 2005, p. U228, XP009106044, ISSN: 0065-7727.

\* cited by examiner

US 9,150,850 B2

COMPOSITIONS AND METHODS FOR ANALYZING PROTEIN INTERACTIONS

The present invention claims priority to U.S. Provisional Patent Application No. 60/710,597 filed Aug. 22, 2005, hereby incorporated by reference in its entirety.

FIELD OF THE INVENTION

The present invention relates to compositions and methods for analyzing and modulating (e.g., enhancing or inhibiting) protein-protein interactions. In particular, compositions and methods of the present invention find use in identifying, reconstituting and characterizing protein-protein interactions, identifying binding subunits, and drug screening. The methods and compositions of the invention may also be used to identify agents that may agonize or antagonize a protein-protein interaction (e.g., using a test compound).

BACKGROUND OF THE INVENTION

Most biological functions are the result of interactions among molecules such as proteins, DNA, RNA and other small molecules. The large-scale analysis of proteins and their interactions, commonly referred to as proteomics, has become one of the most important disciplines for characterizing gene function, for building functional linkages between protein molecules, and for providing insight into the mechanisms of biological processes in a high-throughput mode.

A number of protein expression systems have been used as tools in biochemical research to analyze protein-protein interactions (e.g., antigen-antibody interactions and receptor-ligand binding). These expression systems include genetically engineered cell lines that over-express a protein of interest (e.g., receptor, antibody or enzyme) in modified bacteria, and phage display libraries of multiple proteins. Proteins prepared through these approaches can be isolated and either screened in solution or attached to a solid support for screening against a target of interest such as other proteins, receptor ligands, small molecules, and the like. Recently, a number of researchers have focused their efforts on the formation of arrays of proteins similar in concept to the nucleotide biochips currently being marketed. For example, WO 00/04389 and WO 00/04382 describe microarrays of proteins and protein-capture agents formed on a substrate having an organic thinfilm and a plurality of patches of proteins, or protein-capture agents. Also, WO 99/40434 describes a method of identifying antigen/antibody interactions using antibody arrays and identifying the antibody to which an antigen binds.

While arrays of proteins, and protein-capture agents provide a method of analysis distinct from nucleotide biochips, the preparation of such arrays requires purification of the proteins used to generate the array. Additionally, detection of a binding or catalytic event at a specific location requires either knowing the identification of the applied protein, or isolating the protein applied at that location of the array and determining its identity. Also, attachment of proteins to an array sometimes causes these proteins to lose their ability to interact with other proteins or ligands after immobilization.

What is needed is a means to identify protein binding events wherein a protein or portion thereof (e.g., bait polypeptide) is presented to a protein or portion thereof (e.g., prey polypeptide) in a way that provides a fast, high-throughput and reliable way to monitor protein-protein interactions and in which the proteins retain the ability to interact with other proteins. Additionally, it would be preferable to have the protein presented in a manner that allows for efficient isolation and/or identification of the proteins for which binding events are detected (e.g., identification of prey protein/polypeptide). Finally, the system should enable rapid analysis of the proteins by coupling of the arrays to detection systems that allow for the rapid, high-throughput analysis of chemical or biological samples. Such techniques would be valuable in identifying protein-protein interactions, subunits in multi-subunit complexes, as well as test compounds that may alter (e.g., enhance or inhibit) the protein-protein interaction.

SUMMARY OF THE INVENTION

The present invention relates to compositions and methods for analyzing and modulating (e.g., enhancing or inhibiting) protein-protein interactions. In particular, compositions and methods of the present invention find use in identifying, reconstituting and characterizing protein-protein interactions, identifying binding subunits, and drug screening. The methods and compositions of the invention may also be used to identify agents that may agonize or antagonize a protein-protein interaction (e.g., using a test compound).

Accordingly, in some embodiments, the present invention provides a method for detecting interaction between a first test polypeptide and a second test polypeptide comprising: producing in a host cell a first fusion protein and a second fusion protein, the first fusion protein comprising a Tat signal sequence and the first test polypeptide, the second fusion protein comprising a marker protein and the second test polypeptide; monitoring growth of the host cell under selective pressure; and correlating growth of the host cell with the ability of the first polypeptide and the second polypeptide to interact. In some embodiments, the presence of growth of the host cell is indicative of interaction between the first test polypeptide and the second test polypeptide. In some embodiments, the selective pressure comprises exposure to an antibiotic. In some embodiments, the antibiotic is ampicillin. In some embodiments, the producing comprises introducing into the host cell a first nucleic acid encoding the first fusion protein and a second nucleic acid encoding the second fusion protein; and expressing the nucleic acid sequences in the host cell. In some embodiments, the host cell is $E.\ coli$. In some embodiments, the $E.\ coli$ is $E.\ coli$ strain MC4100. The present invention is not limited by the type of host cell utilized. For example, any bacterial cell may be used including, but not limited to, $E.\ coli$ K12 and its derivatives, $E.\ coli$ B and its derivatives, $E.\ coli$ MG1655 and its derivatives, $E.\ coli$ X1776 or W3110 (e.g., F-, λ-, or prototrophic,) $E.\ coli$ MC4100 derivatives such as B0D, B1LK0, DADE, JARV16, $E.\ coli$ LE392, and RR1; bacilli such as $Bacillus\ subtilis$; and other enterobacteriaceae such as $Salmonella\ typhimurium$, $Serratia\ marcescens$, and various $Pseudomonas$ species or any species of bacteria from the group comprising $Acetobacter$, $Actinomyces$, $Aerobacter$, $Agribacterium$, $Azotobacter$, $Bacillus$, $Bacteroides$, $Bordetella$, $Brucella$, $Chlamydia$, $Clostridium$, $Corynebacterium$, $Erysipelothrix$, $Escherichia$, $Francisella$, $Fusobacterium$, $Haemophilus$, $Klebsiella$, $Lactobacillus$, $Listeria$, $Mycobacterium$, $Myxococcus$, $Neisseria$, $Nocardia$, $Pasteurella$, $Proteus$, $Pseudomonas$, $Rhizobium$, $Rickettsia$, $Salmonella$, $Serratia$, $Shigella$, $Spirilla$, $Spirillum$, $Staphylococcus$, $Streptococcus$, $Streptomyces$, $Trepanema$, $Vibrio$, and $Yersinia$. In some embodiments, at least one of the first test polypeptide and the second test polypeptide comprises prokaryotic polypeptide sequences. In some embodiments, at least one of the first test polypeptide and the second test polypeptide comprises eukaryotic polypeptide sequences. The present invention is not limited by the type of first test polypeptide. Indeed, a variety of first test polypeptides may be utilized in the present invention. In some embodiments, the first test polypeptide is an antibody. In some embodiments, the first test polypeptide is a single chain Fv antibody fragment. In some embodiments, the first test polypeptide is a hormone receptor or a ligand for a hormone receptor. In some embodiments, the hormone receptor is a nuclear hormone receptor. In some embodiments, the first test polypeptide is selected from the group comprising, but not limited to, cytokines, growth factors, oncoproteins, transcription factors and other proteins described herein. In some embodiments, the second test polypeptide comprises polypeptide sequence from a peptide library. In some embodiments, the Tat signal sequence is ssTorA. The present invention is not limited by the type of Tat signal sequence. Indeed, a variety of Tat signal sequences may be utilized including, but not limited to, CueO, DmsA, FdnG, FdoG, HyaA, NapA, SufI, WcaM, YagT, YcbK, YcdB, YdhX, and YnfE. In some embodiments, the marker protein is β-lactamase. The present invention is not limited by marker sequence utilized. Indeed, a variety of marker sequences may be utilized including, but not limited to, a streptomycin phosphotransferase, a neomycin phosphotransferase, a hygromycin phosphotransferase, a protein encoded by the aada gene, a protein encoding resistance to ampicillin, a protein encoding resistance to tetracycline, a protein encoding resistance to chloramphenicol, alkaline phosphatase, β-galactosidase, β-glucoronidase, chloramphenicol acetyl transferase (CAT), dihydrofolate reductase, luciferase, a fluorescent protein, and portions or genetic variants thereof. In some embodiments, the host cell further comprises a test compound. The present invention is not limited by the type of test compound. Indeed, a variety of test compounds, described herein, may be analyzed using the compositions and methods of the present invention. In some embodiments, a change in the growth of host cell in the presence of the test compound, compared to the growth of the host cell in the absence of the test compound, is indicative of the test compound's ability to alter the interaction between the first test polypeptide and the second test polypeptide.

The present invention also provides a composition comprising a cell, wherein the cell comprises a first nucleic acid sequence and a second nucleic acid sequence, the first nucleic acid sequence encoding a polypeptide sequence comprising a first and second region, the first region comprising a Tat signal sequence and the second region comprising a first test polypeptide, and the second nucleic acid sequence encoding a second polypeptide sequence comprising a first and second region, the first region comprising a marker protein and the second region comprising second test polypeptide. In some embodiments, the Tat signal sequence is ssTorA. In some embodiments, the first test polypeptide comprises a bait polypeptide. In some embodiments, the second test polypeptide comprises a prey polypeptide. In some embodiments, the first test polypeptide is Aβ42. In some embodiments, the first test polypeptide is a hormone receptor. In some embodiments, the second test polypeptide is an antibody. In some embodiments, the antibody is an antibody fragment. In some embodiments, the antibody fragment is selected from the group comprising a single-chain Fv fragment (scFv), single-chain antibody (scAb), and $F_{AB}$ antibody fragment. In some embodiments, the antibody is an intracellular antibody. In some embodiments, the intracellular antibody is selected from a combinatorial library of human scFv antibody fragments. In some embodiments, the marker protein is B-lactamase.

The present invention also provides a kit comprising a first nucleic acid sequence and a second nucleic acid sequence, the first nucleic acid sequence encoding a polypeptide sequence comprising a first and second region, the first region comprising a Tat signal sequence and the second region comprising a first test polypeptide, and the second nucleic acid sequence encoding a second polypeptide sequence comprising a first and second region, the first region comprising a marker protein and the second region comprising a second test peptide. In some embodiments, the first nucleic acid sequence and the second nucleic acid sequence are present within a cell. In some embodiments, the cell is an *E. coli* cell.

The present invention also provides a method for detecting interaction between a first test polypeptide and a second test polypeptide comprising producing in a host cell a first fusion protein and a second fusion protein, the first fusion protein comprising a Tat signal sequence and the first test polypeptide, the second fusion protein comprising a marker protein and the second test polypeptide; and detecting extra-cytoplasmic presence of a first test polypeptide:second test polypeptide heterodimeric complex. In some embodiments, the detecting comprises monitoring growth of the host cell under selective pressure; and correlating growth of the host cell with the ability of the first polypeptide and the second polypeptide to interact. In some embodiments, detecting comprises using any one of a number of biological screening assays well known to those of skill in the art including, but not limited to, cell-free assay, fluorescence resonance energy transfer (FRET), real-time Biomolecular Interaction Analysis (BIA) and Western blotting.

DEFINITIONS

Figure 1:
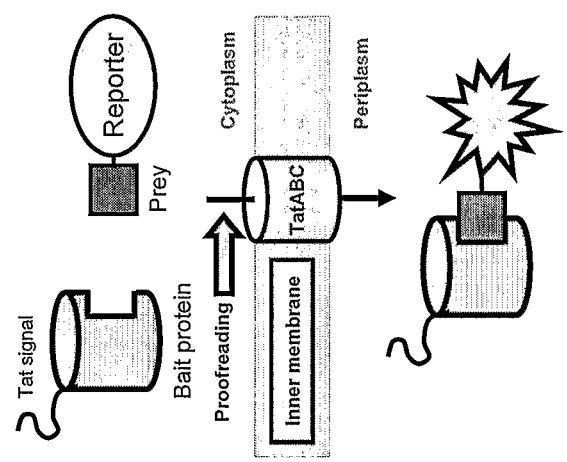
FIG. 1 shows a schematic of one embodiment of a TRAP assay of the present invention for detecting protein interaction.

To facilitate an understanding of the invention, a number of terms are defined below.

As used herein, the terms "polypeptide," "protein," and "peptide" are used interchangeably to refer to amino acid chains in which the amino acid residues are linked by covalent peptide bonds. The amino acid chains can be of any length of at least two amino acids, including full-length proteins. Unless otherwise specified, the terms "polypeptide," "protein," and "peptide" also encompass various modified forms thereof, including but not limited to glycosylated forms, phosphorylated forms, PEGylated forms, etc.

As used herein, the terms "bait polypeptide," "prey polypeptide" and "bait/prey polypeptide" refers to a chemical compound, preferably an organic compound, to be tested in the present invention to determine its ability to interact with another chemical compound. In a preferred embodiment, the bait/prey polypeptides are polypeptides, in which case the bait/prey polypeptides comprise a sequence of amino acids (e.g., encoding an entire protein or a portion of the protein (e.g., from about two amino acids to one amino acid less than the entire protein). Accordingly, as used herein, the term "test polypeptide" refers to "bait polypeptides" and/or "prey polypeptides." The terms "bait polypeptides" and/or "prey polypeptides" also refer to a polypeptide or nucleic acid encoding a polypeptide of interest for which protein-protein interaction is to be analyzed and/or altered of the present invention. The terms encompass both wild-type proteins and those that are derived from wild type proteins (e.g., variants of wild-type proteins or polypeptides, or, chimeric genes constructed with portions of target protein coding regions), and further encompass fragments of a wild-type protein as well as other domains (e.g., within the full-length protein or nucleotide sequence). Thus, in some embodiments, a "bait polypeptide" or "prey polypeptide" is a variant or mutant. The present invention is not limited by the type of bait polypeptides and prey polypeptides analyzed. The terms "bait polypeptide nucleotide sequence" and "prey polypeptide nucleotide sequence" are meant to encompass DNA, cDNA, and RNA (e.g., mRNA) sequences.

The term "fusion protein" refers to a non-naturally occurring hybrid or chimeric protein having two or more distinct portions covalently linked together, each portion being or being derived from a specific molecule, and also refers to the nucleic acid sequence encoding the same.

As used herein, the terms "interacting" or "interaction" refer to two domains or independent entities (e.g., test polypeptides (e.g., bait and/or prey polypeptides) that exhibit sufficient physical affinity to each other so as to bring the two "interacting" domains or entities physically close to each other. An extreme case of interaction is the formation of a chemical bond that results in continual, stable proximity of the two domains. Interactions that are based solely on physical affinities, although usually more dynamic than chemically bonded interactions, can be equally effective at co-localizing independent entities. Examples of physical affinities and chemical bonds include but are not limited to, forces caused by electrical charge differences, hydrophobicity, hydrogen bonds, van der Wals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between antigen and antibody, ligand and receptor, and the like. An "interaction" between two protein domains, fragments or complete proteins can be determined using the methods of the present invention.

The invention is not limited by the type of marker protein. As used herein, the terms "marker protein" or "selectable marker" refer to a nucleic acid sequence (e.g., gene) that encodes an activity (e.g., an enzymatic activity) that confers the ability to grow in medium lacking what would otherwise be an essential nutrient (e.g. the HIS3 gene in yeast cells); in addition, a "marker protein" or "selectable marker" may confer resistance to an antibiotic or drug upon the cell in which the selectable marker is expressed. The present invention contemplates the use of a marker protein or selective marker in plasmids comprising nucleic acid sequences encoding a fusion protein, as well as use of a marker protein or selective marker within the nucleic acid sequence encoding the fusion protein itself. For example, host cells comprising a nucleic acid encoding a fusion protein may grow in a selective environment (e.g., when exposed to an antibiotic) because the nucleic acid encoding a fusion protein (e.g., comprising a marker protein) encodes activity (e.g., β-lactamase activity) that confers resistance to the antibiotic.

As used herein, the term "instructions for using said kit for monitoring protein-protein interaction" includes instructions for using the reagents contained in the kit for monitoring the ability of a prey polypeptide to interact with a bait polypeptide (e.g., through the growth of host cells in the presence of a selectable marker).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of a sample (e.g., a nucleic acid encoding a fusion protein of the present invention) to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics (e.g., increased or decreased solubility) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_M$" as used herein refers to the Michaelis-Menton constant for an enzyme and is defined as the concentration of the specific substrate at which a given enzyme yields one-half its maximum velocity in an enzyme catalyzed reaction.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are 20 amino acids long, usually at least 50 amino acids long or longer, and span the portion of the polypeptide required for intermolecular binding of the compositions (claimed in the present invention) with its various ligands and/or substrates.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (e.g., 10 nucleotides, 20, 30, 40, 50, 100, 200, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. The present invention is not limited to naturally occurring protein molecules. For example, the present invention contemplates synthesis of fusion proteins comprising multiple regions of unique polypeptide sequences (e.g., a Tat signal sequence, a target protein sequence, and marker protein sequence).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "native protein" is used to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to alter (e.g., enhance or inhibit) the interaction between two or more molecules (e.g., peptides or proteins (e.g., the interaction of which is characterized using the compositions and methods of the present invention)). Test compounds comprise both known and potential therapeutic compounds. A test compound can be determined to be therapeutic by screening using the screening methods of the present invention. Examples of test compounds include, but are not limited to, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, drug, antibody, prodrug, antibodies or portions thereof (e.g., antibody fragments), glycopeptides, glycoproteins, proteoglycans and the like, and synthetic analogues or derivatives thereof, including peptidomimetics, small molecule organic compounds and the like, and mixtures thereof (e.g., that is a candidate for use to alter (e.g., enhance or inhibit) the interaction between two or more molecules (e.g., peptides or proteins (e.g., the interaction of which is characterized using the compositions and methods of the present invention)). It is to be understood that test compounds comprise both known and potential interaction inhibiting or enhancing agents. A test compound can be determined to be capable of altering protein-protein interaction using a method of the present invention. Thus, test compounds comprise both known and potential therapeutic compounds. A test compound can be determined to be therapeutic by screening using the screening methods of the present invention.

As used herein, the term "test compound library" refers to a mixture or collection of one or more compounds generated or obtained in any manner. Preferably, the library contains more than one compound or member. The test compound libraries employed in this invention may be prepared or obtained by any means including, but not limited to, combinatorial chemistry techniques, fermentation methods, plant and cellular extraction procedures and the like. Methods for making combinatorial libraries are well-known in the art (See, for example, E. R. Felder, Chimia 1994, 48, 512-541; Gallop et al., J. Med. Chem. 1994, 37, 1233-1251; R. A.

Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Each of these references is incorporated herein by reference in its entirety).

The term "synthetic small molecule organic compounds" refers to organic compounds generally having a molecular weight less than about 1000, preferably less than about 500, which are prepared by synthetic organic techniques, such as by combinatorial chemistry techniques.

As used herein the term "prodrug" refers to a pharmacologically inactive derivative of a parent "drug" molecule that requires biotransformation (e.g., either spontaneous or enzymatic) within the target physiological system to release, or to convert (e.g., enzymatically, mechanically, electromagnetically, etc.) the "prodrug" into the active "drug." "Prodrugs" are designed to overcome problems associated with stability, toxicity, lack of specificity, or limited bioavailability. Exemplary "prodrugs" comprise an active "drug" molecule itself and a chemical masking group (e.g., a group that reversibly suppresses the activity of the "drug"). Some preferred "prodrugs" are variations or derivatives of compounds that have groups cleavable under metabolic conditions. Exemplary "prodrugs" become pharmaceutically active in vivo or in vitro when they undergo solvolysis under physiological conditions or undergo enzymatic degradation or other biochemical transformation (e.g., phosphorylation, hydrogenation, dehydrogenation, glycosylation, etc.). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

As used herein; the term "drug" refers to a pharmacologically active molecule that is used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather than a particular structure such as an epitope).

As used herein, the term "host cell" refers to any cell, whether located in vitro or in vivo, that can be, or has been, a recipient for or incorporates exogenous nucleic acid sequences (e.g., vectors comprising fusion protein sequence), polynucleotides and/or proteins of the present invention. It is also meant to include progeny of a single cell, and the progeny may not necessarily be completely identical (e.g., in morphology or in genomic or total DNA complement) to the original parent cell due to natural, accidental, or deliberate mutations. The cells may be eukaryotic or prokaryotic and include, but are not limited to bacterial cells (e.g., *E. coli*), yeast cells, mammalian cells, avian cells, amphibian cells, plant cells, fish cells, and insect cells).

DETAILED DESCRIPTION OF THE INVENTION

In bacterial cells, specific targeting and transport mechanisms are required to move proteins along transport pathways from their site of synthesis in the cytoplasm to their eventual destination. One such pathway, the twin-arginine translocation (Tat) pathway, is capable of delivering folded proteins across biological membranes via translocation machinery minimally comprised of the TatABC proteins (See, e.g., Berks, Mol Microbiol 22, 393-404 (1996); Settles et al., Science 278, 1467-1470 (1997); Weiner et al., Cell 93, 93-101

(1998)). Recent in vivo studies demonstrate the ability of the Tat pathway to selectively discriminate between properly folded and misfolded proteins in vivo and suggest the existence of a folding quality control mechanism intrinsic to the process (See, e.g., Sanders et al., Mol Microbiol 41, 241-246 (2001); Lutz et al., Protein Eng 15, 1025-1030 (2002); DeLisa et al., Proc Natl Acad Sci USA 100, 6115-6120 (2003)).

In some embodiments, the present invention exploits the Tat pathway and provides a general platform for screening protein-protein interaction.

Several diseases, such as Alzheimer's disease, Parkinson's disease, Huntington's disease, and others (e.g., tauopathies in general) are thought to be the result of, or associated with protein misfolding in vivo. In some embodiments, the present invention provides a method for assaying for protein-protein interactions that assist or inhibit protein folding and/or misfolding in a living cell (e.g., a bacterial cell).

In some embodiments, the present invention provides compositions and methods for analyzing and modulating (e.g., enhancing or inhibiting) protein-protein interactions. In particular, compositions and methods of the present invention find use in identifying, reconstituting and analyzing protein-protein interactions, identifying binding subunits, and drug screening. The methods and compositions of the invention may also be used to identify agents that may agonize or antagonize a protein-protein interaction (e.g., using test compounds).

Accordingly, in some embodiments, the present invention provides compositions and methods that utilize the twin-arginine translocation (Tat) pathway for detecting protein-protein interactions directly in living cells. Thus, in some embodiments, the present invention provides a facile route to the high-throughput identification of interacting proteins. As such, in some embodiments, the present invention provides compositions and methods useful in the discovery of drug targets and also the discovery of drugs directly.

In some embodiments, the present invention utilizes the hitchhiker and proofreading capabilities of the *Escherichia coli* twin-arginine translocation (Tat) pathway, to detect interacting proteins in vivo (See, e.g., FIG. 1). In some embodiments, molecular cloning techniques can be used as tools to clone any protein of interest (bait polypeptide), e.g. protein or peptide antigen into a plasmid containing a Tat signal peptide (e.g., ssTorA), which can be used to screen for high affinity interacting protein partners (prey polypeptides—e.g., an scFv antibody fragment expressed from a large non-immune combinatorial library) fused to a marker protein (e.g., an antibiotic marker protein such as β-lactamase). Thus, in some embodiments, the present invention provides a high-throughput, inexpensive, and reliable method to study protein-protein interactions. For example, using a marker protein (e.g., β-lactamase) greatly simplifies the screening of large libraries as it confers upon bacteria the ability to grow on nutrient agar plates containing antibiotics (e.g., β-lactam antibiotics such as ampicillin and carbenicillin). Although an understanding of the mechanism is not necessary to practice the present invention and the present invention is not limited to any particular mechanism of action, in some embodiments, since a protein (e.g., bait protein) is fused (e.g., transcribed and translated together) to a signal sequence (e.g., ssTorA signal peptide) and another peptide (e.g., prey peptide) is fused (e.g., transcribed and translated together) to a marker protein (e.g., β-lactamase protein), transport of the heterodimeric complex (e.g., associated via protein-protein interactions) throughout (e.g., from the cytoplasmic space to the periplasmic space) the host cell (e.g., *E. coli*) results in growth of the host cells within a selective environment (e.g., on plates containing antibiotics (e.g., ampicillin)). Using growth as a selection, the protein partners can be facilely isolated, identified, and characterized (e.g., sequenced, characterized biochemically, etc.).

Although an understanding of the mechanism is not necessary to practice the present invention and the present invention is not limited to any particular mechanism of action, in some embodiments, protein-protein interactions are detected utilizing the Tat pathway's ability to transport folded protein complexes (See, e.g., DeLisa et al., (2003) *Proc Natl Acad Sci USA* 100, 6115-6120; Rodrigue et al., (1999) *J Biol Chem* 274, 13223-13228). This technology mimics the hitchhiker mechanism of the natural Tat substrates, for example, HybO and HybC. HybO and HybC are the small and large subunits of hydrogenase 2 (Hyd2) of *E. coli*, respectively. HybO contains an N-terminal twin-arginine signal peptide while HybC has no known targeting signal for export. Previous studies have shown that the two subunits assemble in the cytoplasm prior to Tat transport and, following assembly into a HybOC heterodimeric complex, are efficiently transported to the periplasm by virtue of the HybO signal peptide. Characterization of this pathway has provided that the Tat system is capable of transporting heterodimeric protein complexes whereby only one protein carries a Tat targeting signal (See, e.g., Examples 2-5).

Thus, in some embodiments, the present invention provides a composition comprising a Tat signal sequence (e.g., ssTorA) fused to a sequence encoding a protein of interest (e.g., a bait or prey polypeptide) and cloning the gene fusion into an expression vector (e.g., an *E. coli* expression vector). Nucleic acid sequence encoding a second protein (e.g., a bait or prey polypeptide) can be fused to a Tat-compatible marker protein (e.g., β-lactamase) and cloned into a second expression vector. In some embodiments, the plasmids are co-expressed (e.g., co-transfected) in a host cell (e.g., a bacterial cell (e.g., *E. coli*.)).

The present invention is not limited by the type of marker protein utilized. Indeed a variety of marker proteins are contemplated to be useful in the present invention including, but not limited to, a FLASH tag, a streptomycin phosphotransferase, a neomycin phosphotransferase, a hygromycin phosphotransferase, a protein encoded by the aada gene, proteins encoding resistance to ampicillin, tetracycline, or chloramphenicol, alkaline phosphatase, β-galactosidase, β-glucoronidase, chloramphenicol acetyl transferase (CAT), DHFR, luciferase, a fluorescent protein, and portions or genetic variants thereof. One advantage of β-lactamase is that it is a monomeric protein of relatively small size, and can be fused to other proteins and retain activity (See, e.g., Moore et al., (1997) *Anal Biochem* 247, 203-209).

In some embodiments, both vectors are co-transferred (e.g., transformed, transfected, co-expressed, etc.) into host cells (e.g., bacteria (e.g., *E. coli*)) whereby expression of the test polypeptides (e.g., bait and prey polypeptides) is induced (e.g., using an inducible promoter known in the art (e.g., IPTG or tetracycline inducible promoter)). When expressed in the host cells, if the test polypeptides (e.g., bait and prey) interact with each other, then a heterodimeric complex (e.g., a Tat signal sequence-bait::prey-marker protein) will form in the cytoplasm, establishing a linkage between the Tat signal sequence and marker protein. In some embodiments, a ssTorA signal-Bait::Prey-β-lactamase protein complex is formed (See, e.g., Examples 2-5). Although an understanding of the mechanism is not necessary to practice the present invention and the present invention is not limited to any particular mechanism of action, in some embodiments, the complex is co-translocated to the periplasm where marker protein (e.g., β-lactamase) is active against antibiotic (e.g., ampicillin) present within the plate rendering the host cells (e.g., *E. coli* cells) resistant to the antibiotic. Cells carrying interacting proteins can simply and reliably be identified (e.g., by plate selection or other growth characteristic (e.g., optical density)). In the absence of an interaction, the marker protein (e.g., β-lactamase) will remain localized in the cytoplasm and cells will be sensitive to the selective pressure (e.g., antibiotics) present within the plate. In some embodiments, a vector comprising a nucleic acid sequence encoding a first or second polypeptide sequence also comprises one or more other regions of nucleic acid that can be attached to nucleic acid sequence encoding the first or second polypeptide sequence. The present invention is not limited by the type of one or more other region of nucleic acid that may comprise, but not be limited to, linker regions, enhancers, promoters, non-coding sequences, and other types of sequences described herein.

In some embodiments, combinatorial gene libraries are screened by cloning libraries (e.g., DNA libraries) into the bait and/or prey position. The ability of clones within this library to bind to a target of interest (e.g., bait and/or prey polypeptide) can be readily screened by plating cells on antibiotic (e.g., ampillicin)-containing agar plates. Although an understanding of the mechanism is not necessary to practice the present invention and the present invention is not limited to any particular mechanism of action, in some embodiments, the quality control feature of the Tat system is an advantage of the genetic selection scheme of the present invention as misfolded complexes will be rejected by the Tat transporter, thus reducing false positives arising from the interaction of misfolded proteins.

In some embodiments, instead of using full-length marker proteins (e.g., β-lactamase), protein-protein interactions can be monitored and characterized using the complementation of enzyme fragments. An advantage of this approach is that it may reduce false positives caused by "leakage" of full-length marker protein (e.g., β-lactamase) into the periplasm or surrounding medium in the absence of any protein-protein interaction. For example, complementation of β-lactamase enzyme fragments, α197 and ω198, have been used to detect protein-protein interactions in *E. coli* and mammalian cells (See, e.g., Wehrman et al., (2001) *Proc Natl Acad Sci USA* 99, 3469-3474). Thus, in some embodiments, it is contemplated that the compositions and methods of the present invention utilize portions of marker proteins (e.g., based on α197 and ω198 fragments of β-lactamase). Thus, in some embodiments, a nucleic acid comprising a Tat signal sequence operatively linked to a bait polypeptide may also be operatively linked to an inactive fragment of a marker protein, wherein this nucleic acid sequence is co-expressed in a host cell with a second nucleic acid sequence encoding a prey polypeptide operatively linked to another inactive fragment of the marker protein, wherein when co-expressed, the marker protein is active (e.g., provides resistance to an antibiotic). An assay based on the complementation of enzyme fragments is highly sensitive and reduces background that may occur when using the full-length enzyme (e.g., that might leak into the periplasm due to non-specific transport, or into the medium due to cell lysis).

One aspect of the present invention is the discovery that multiple (e.g., two or more) peptides, polypeptides or proteins (e.g., bait and prey polypeptides) may be expressed in a host cell wherein protein-protein interaction of the expressed polypeptides is monitored by the growth, or lack of growth, of host cells comprising the expressed polypeptides. The bait and/or prey polypeptides may have the same length of amino acid sequence as the endogenously produced protein, if such protein exists. In other embodiments, the bait and/or prey polypeptide may be a truncated protein, protein domain or protein fragment of a larger peptide chain. For example, the bait and/or prey polypeptide may comprise a fragment of a membrane embedded or otherwise hydrophobic protein.

In some embodiments, fusion proteins are produced by operatively linking at least one nucleic acid encoding at least one amino acid sequence to at least a second nucleic acid encoding at least a second amino acid sequence, so that the encoded sequences are translated as a contiguous amino acid sequence either in vitro or in vivo. Fusion protein design and expression is well known in the art, and methods of fusion protein expression are described herein, and in references, such as, for example, U.S. Pat. No. 5,935,824, incorporated herein by reference in its entirety for all purposes. In some embodiments, linkers are used to join the various portions of the fusion protein. One such linker is another peptide, such as described in U.S. Pat. No. 5,990,275, incorporated herein by reference in its entirety for all purposes. In some embodiments, a first fusion protein, and nucleic acids encoding the same, comprises a Tat signal sequence and a test polypeptide (e.g., Alzheimer Aβ42 peptide), and a second fusion protein comprises an antibiotic resistance marker and a test polypeptide (e.g., an antibody or antibody fragment). It is contemplated that the portions of the fusion proteins may be assembled in any order (e.g., the bait and/or prey polypeptide is to the N- or C-terminus of the Tat and/or marker protein).

An important class of protein-protein and protein-peptide interactions is antibody-antigen interactions. Accordingly, in some embodiments, the present invention discloses methods of identifying (e.g., isolating) intracellular antibodies (e.g., intrabodies) that are specific for certain intracellular molecules. In some embodiments, the identified intrabodies are able to alter (e.g., block, suppress, or even enhance) the processes mediated by those molecules. In some embodiments, an intracellular antibody identified using the compositions and methods of the present invention is used as a therapeutic and/or diagnostic reagent (e.g., for cancer, neurodegenerative disease, or other disorder). Thus, the present invention provides a method of identifying and characterizing molecules (e.g., test compounds) that can be used as therapeutic reagents.

An indication of the significance of antibody therapeutics is that over 30% of biopharmaceuticals in clinical trials, as highlighted by recent approvals from FDA, are engineered antibodies (See, e.g., Hundson and Souriau, (2003) Engineered Antibodies. *Nat. Med.* 9, 129-134). As the human body naturally invokes an immune response when exposed to foreign proteins, generation of antibody therapeutics requires protein engineering to reduce immunogenicity and increase antigen affinity. Thus, in some embodiments, the present invention provides a method to screen a combinatorial library of human proteins or polypeptide sequences (e.g., scFv sequences) for identification and/or isolation of intracellular antibodies. In some embodiments, the intracellular antibodies are stably expressed in the cytoplasm of cells. In some embodiments, the intracellular antibodies exhibit high affinity towards target molecules, particularly those associated with human disease (e.g., a neurodegenerative disease (e.g., Aβ42, the 42 amino acid long amyloid β-peptide related to Alzheimer's disease and other tauopathies (e.g., including, but not limited to Pick's disease (PiD), progressive supranuclear palsy, corticobasal degeneration, argyrophilic grain disease or familial frontotemporal dementia and parkinsonism linked to chromosome 17 due to mutations in the tau gene (FTDP-17-tau)).

In some embodiments, using the compositions and methods of the present invention, proteins (e.g., antibodies) are identified and characterized that can alter (e.g., enhance or inhibit) protein folding (e.g., of protein associated with diseases (e.g., human disease such as Alzheimer's disease, other tauopathy, cancer, or other type of disease). For example, Alzheimer's disease (AD) is one of several diseases (e.g., tauopathies) in which the formation of protein clumps is important. Various C-terminally truncated amyloid β peptides, such as Aβ42, are linked to AD pathogenesis with deposition of Aβ42 in the brain considered as central to AD pathology. Thus, in some embodiments, proteins (e.g., antibodies) can be identified and characterized using the compositions and methods of the present invention that stabilize or enhance folding of Aβ42 and thus inhibit its agglomeration and prevent Aβ plaques from forming.

The present invention is not limited by the type of test polypeptides (e.g., bait and/or prey polypeptides) assayed, nor to the type of Tat signal peptide or marker protein used. Indeed, the present invention can be utilized to characterize or monitor the protein-protein interaction of any protein, and the ability of other factors (e.g., test compounds (e.g., small molecules, pharmaceuticals, etc.)) to alter (e.g., enhance or inhibit) the interaction.

In some embodiments, a test polypeptide (e.g., a bait and/or prey polypeptide) is an antibody or antibody fragment. The present invention is not limited by the type of antibody or antibody fragment. Indeed, a variety of antibodies or antibody fragments may be used in the compositions and methods of the present invention including, but not limited to, all varieties of single chain antibody fragments (e.g., Fab, $Fab_2$ (bispecific), $Fab_3$ (trispecific) scAb, scFv, Bis-scFv, Diabody, Triabody, Minibody, Tetrabody, Transbody, ADEPT molecule (scFv-enzyme fusion), immunotoxin, VhH domain, V-NAR domain, $V_H$ domain, $V_L$ domain, Camel Ig, IgNAR, and IgG). In addition, a test polypeptide (e.g., a bait and/or prey polypeptide) may be selected from the group comprising single chain T cell receptor ligands (scTCRs); recombinant T cell receptor ligands (RTLs); single-chain class I and II MHC molecules; non-antibody binding proteins (e.g., fluorobodies, peptide aptamers, Affibody, Maxibody, Tetranectin (e.g., C-type lectin), IMabs, AdNectin, Kunitz-type domain from human or bovine trypsin inhibitor, Evibody, ankyrin repeat protein, anticalin (e.g., human lipocalin), affilin molecule (e.g., human gamma-crystallin/human ubiquitin), and Microbody.

In some embodiments, a test polypeptide (e.g., bait and/or prey polypeptide) is a hormone receptor (e.g., a nuclear hormone receptor) or a ligand for a nuclear hormone receptor. Nuclear hormone receptors are grouped into a large superfamily and are thought to be evolutionarily derived from a common ancestor. Seven subfamilies of mammalian nuclear receptors exist. Class I comprises thyroid hormone receptor, retinoic acid receptor, vitamin D receptor, peroxisome proliferator activated receptor, pregnane X receptor, constitutive androstane receptor, liver X receptor, farnesoid X receptor, reverse ErbA, retinoid Z receptor/retinoic acid-related orphan receptor and the ubiquitous receptor. Class II comprises retinoid X receptor, chicken ovalbumin upstream promoter transcription factor, hepatocyte nuclear factor 4, tailless-related receptor, photoreceptor-specific nuclear receptor and testis receptor. Class III comprises glucocorticoid receptor, androgen receptor, progesterone receptor, estrogen receptor and estrogen-related receptor. NGF-induced clone B is a class IV nuclear receptor; steroidogenic factor 1 and Fushi Tarazu factor 1 are class V receptors; germ cell nuclear factor is a class VI receptor; and, small heterodimeric partner and dos-age-sensitive sex reversal are class 0 receptors (See, e.g., Aranda and Pascual, Physiol Rev. 2001, 81(3):1269-1304).

Ligands for some of these types of receptors have been identified, for example, products of lipid metabolism such as fatty acids, prostaglandins, or cholesterol derivatives have been shown to regulate gene expression by binding to nuclear receptors. These nuclear receptors bind to hormone response elements as monomers, homodimers, or RXR heterodimers. Ligands may play a role in dimerization and binding to DNA (See, e.g., Ribeiro, Kidney Int. 1992, 42(6):1470-83). A number of proteins interact with these receptors, including general transcription factors. As with other transcriptional regulatory proteins, one aspect of the mechanisms by which nuclear receptors affect the rate of RNA polymerase II-directed transcription likely involves the interaction of receptors with components of the transcription preinitiation complex. This interaction may be direct, or it may occur indirectly through the action of bridging factors (See, e.g., Schulman, Curr Opin Neurobiol. 1995, (3):375-81). Sequence-specific transcription factors, coactivators and corepressors (See, e.g., Cavailles et al., 1995, EMBO J. 1995 Aug. 1; 14(15):3741-51) also have been found to interact with these nuclear receptors. Thus, in some embodiments, compositions and methods of the present invention are useful for identifying nuclear hormone receptors and their ligands. For example, in some embodiments, compositions and methods of the present invention are used to identify agents (e.g., test compounds/candidate compounds) that alter (e.g., enhance or inhibit) ligand binding to nuclear hormone receptors.

Voltage-dependent calcium channels mediate the entry of calcium into neurons and other excitable cells and play important roles in a variety of neuronal functions, including membrane excitability, neurotransmitter release, and gene expression. Calcium channels are multisubunit complexes with the channel activity mainly mediated by the pore-forming subunit; however, additional subunits act as accessory proteins that regulate channel activity (See, e.g., Catterall, 1995, Annu Rev Biochem. 1995; 64:493-531). In some embodiments, compositions and methods of the present invention are useful for identifying proteins or subunits of proteins that are associated with voltage dependent channels (e.g., calcium and sodium channels).

Ubiquitin-mediated protein degradation is a highly selective process that is achieved through the concerted action of a versatile set of enzymes (See, e.g., Hershko and Ciechanover, 1998, Annu Rev Biochem.; 67:425-79; Varshavsky, 1997, Trends Biochem Sci. October; 22(10):383-7). A single E1 enzyme (ubiquitin activating enzyme) is responsible for activation of the small protein ubiquitin, which is then passed on via trans-acetylation to several E2 enzymes (ubiquitin conjugating enzyme). Each E2 may collaborate with several different E3 proteins in creating a protein-ubiquitin conjugate. The E3s, referred to as ubiquitin-protein ligases, confer specificity to the system and share a common property: substrate recognition and binding. Whereas the E2 proteins bear a significant homology to each other, the E3s many of which are associated with large multisubunit complexes, form a highly heterogenous group. Within these complexes the specific task of individual subunits is not always clear (See, e.g., Zachariae and Nasmyth, 1999, Genes Dev.; 13(16):2039-58). Moreover, the composition of the complex is not necessarily static and may be subject to regulatory processes associated with the functional status of the cell (See, e.g., Zachariae et al., 1998, Science, 282(5394):1721-4). Only a few E3s have been characterized in detail and there is only scant information regarding mammalian E3s. Among the latter, one of the better-defined E3s is SCF (beta-TrCP/E3RS), a recently identified E3 complex that targets pIkappaBalpha and beta-catenin for degradation (See, e.g., Karin and Ben-Neriah, 2000, Annu Rev Immunol.; 18:621-63;). Compositions and methods of the present invention are useful for identifying proteins or subunits of proteins that are associated with ubiquitin-mediated protein degradation.

Additional multisubunit complexes are known in the art and described in the literature, and include without limitation, the nuclear pore complex, the ribosome complex, the 26S proteosome complex, the F0F1 ATPase complex, DNA polymerase, and components of the transcriptional initiation complex, which includes RNA polymerase II (which is composed of at least 12 subunits) and TFIID, TFIIB, TFIIA, TFIIF, TFIIE, and TFIIH (See, e.g., Wilson, et al. 1996, Cell. 84(2): 235-44). Also contemplated are complexes comprising one or more nucleic acid molecules. Compositions and methods of the present invention can be used for identifying proteins or subunits of proteins that are associated with these complexes.

Compositions and methods of the present invention can also be used, inter alia, for identifying protein-protein interactions, e.g., for generating protein linkage maps, for identifying therapeutic targets, and/or for general cloning strategies. In some embodiments, bait or prey polypeptides can be derived from a cDNA library to produce a variegated array of bait or prey proteins which can be screened for interaction with, for example, a known protein expressed as a corresponding fusion protein. In other embodiments, both the bait and prey polypeptides can be derived to each provide variegated libraries of polypeptide sequences. One or both libraries can be generated by random or semi-random mutagenesis. For example, random libraries of polypeptide sequences can be "crossed" with one another by simultaneous expression in the subject assay. Such embodiments can be used to identify novel interacting pairs of polypeptides.

Alternatively, compositions and methods of the present invention can be used to map residues of a protein involved in a known protein-protein interaction. Thus, for example, various forms of mutagenesis can be utilized to generate a combinatorial library of either bait or prey polypeptides, and the ability of the corresponding fusion protein to function in assays of the present invention can be assayed (e.g., by monitoring the ability of host cells to grow in a selective environment). Mutations that result in altered (e.g., diminished or potentiated) binding between the bait and prey fusion proteins can be detected by an alteration (e.g., decrease or increase) in host cell viability on an antibiotic containing plate. For example, mutants of a particular protein that alter interaction of that protein with another protein can be generated and isolated from a library created, for example, by alanine scanning mutagenesis and the like (See, e.g., Ruf et al., (1994) Biochemistry 33:1565-1572; Wang et al., (1994) J. Biol. Chem. 269:3095-3099; Balint et al., (1993) Gene 137: 109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (See, e.g., Gustin et al., (1993) Virology 193:653-660; Brown et al., (1992) Mol. Cell Biol. 12:2644-2652; McKnight et al., (1982) Science 232:316); by saturation mutagenesis (See, e.g., Meyers et al., (1986) Science 232:613); by PCR mutagenesis (See, e.g., Leung et al., (1989) Method Cell Mol Biol 1:11-19); or by random mutagenesis (See, e.g., Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying modified (e.g., truncated or otherwise mutated bioactive forms (e.g., bioactive forms) of a protein (e.g., to identify and/or characterize binding domains).

In some embodiments, compositions and methods of the present invention can be designed for the identification and/or characterization of genes encoding proteins that physically interact with a protein/drug complex. For example, in some embodiments, if the bait and prey fusion proteins are able to interact in a drug-dependent manner, the interaction may be detected by host cell growth.

Another aspect of the present invention relates to the use of the interaction trap systems in the development of assays that can be used to screen test compounds that are either agonists or antagonists of a protein-protein interaction of therapeutic consequence (See, e.g., U.S. Pat. No. 6,200,759, hereby incorporated by reference in its entirety). In a general sense, the assay evaluates the ability of a test compound to modulate (e.g., enhance or inhibit) binding between bait and prey polypeptides.

The present invention is not limited by the type of test compound. In some embodiments, the test compound is one of a library of test compounds. The present invention is not limited by the type of test compound assayed (e.g., to identify and characterize test compounds capable of altering (e.g., enhancing or inhibiting) the interaction between two or more molecules (e.g., peptides or proteins (e.g., the interaction of which is characterized using the compositions and methods of the present invention)). Indeed a variety of test compounds can be analyzed by the present invention including, but not limited to, any chemical entity, pharmaceutical, drug, known and potential therapeutic compounds, small molecule inhibitors, pharmaceuticals, a test compound from a combinatorial library (e.g., a biological library; peptoid library, spatially addressable parallel solid phase or solution phase library; synthetic library (e.g., using deconvolution or affinity chromatography selection)), and the like. Examples of test compounds useful in the present invention include, but are not limited to, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, glycopeptides, glycoproteins, antibody and antibody fragments, proteoglycans and the like, and synthetic analogues or derivatives thereof, including peptidomimetics, small molecule organic compounds and the like, and mixtures thereof.

The present invention also provides a method of identifying a test compound that can alter (e.g., enhance or inhibit) the interaction between two or more molecules (e.g., peptides or proteins) comprising administering to a host cell (e.g., comprising a first nucleic acid sequence and a second nucleic acid sequence, the first nucleic acid sequence encoding a polypeptide sequence comprising a first and second region, the first region comprising a Tat signal sequence and the second region comprising a bait polypeptide, and the second nucleic acid sequence encoding a second polypeptide sequence comprising a first and second region, the first region comprising a marker protein and the second region comprising a prey peptide) and monitoring the test compound's ability to alter test cell growth (e.g., under selective pressure (e.g., exposure to antibiotic)).

For example, in some embodiments, an assay is designed to identify and/or characterize a test compound's ability to alter (e.g., enhance or inhibit) the interaction of two polypeptide sequences (e.g., proteins) known to interact (e.g., that interact within a host cell when the proteins are expressed in the host cell (e.g., from a first nucleic acid sequence and a second nucleic acid sequence, the first nucleic acid sequence encoding a polypeptide sequence comprising a first and second region, the first region comprising a Tat signal sequence and the second region comprising a bait polypeptide, and the second nucleic acid sequence encoding a second polypeptide sequence comprising a first and second region, the first region comprising a marker protein and the second region comprising a prey peptide)). In some embodiments, the two polypeptides known to interact are a ligand and a ligand receptor (e.g., a hormone and a hormone receptor, a growth factor and a growth factor receptor, or any other known interaction between two polypeptide (e.g., protein) sequences). In some embodiments, a test compound is identified that can be utilized for treating (e.g., prophylactically and/or therapeutically) a subject.

The test compounds of the present invention can be obtained using any of the numerous approaches in combinatorial library methods known in the art, including biological libraries; peptoid libraries (e.g., libraries of molecules having the functionalities of peptides, but with a novel, non-peptide backbone, which are resistant to enzymatic degradation but which nevertheless remain bioactive; See, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (See, e.g., Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994), each of which is hereby incorporated by reference in its entirety.

The present invention is not limited by the method of presenting (e.g., administering) a test compound to a host cell. For example, a test compound and/or libraries of compounds may be presented in solution (See, e.g., Houghten, Biotechniques 13:412-421 (1992)), or on beads (See, e.g., Lam, Nature 354:82-84 (1991)), chips (See, e.g., Fodor, Nature 364:555-556 (1993)), bacteria or spores (See, e.g., U.S. Pat. No. 5,223,409; herein incorporated by reference), plasmids (See, e.g., Cull et al., Proc. Nad. Acad. Sci. USA 89:18651869 (1992)) or on phage (See, e.g., Scott and Smith, Science 249:386-390 (1990); Devlin Science 249:404-406 (1990); Cwirla et al., Proc. Natl. Acad. Sci. 87:6378-6382 (1990); Felici, J. Mol. Biol. 222:301 (1991)).

In addition to monitoring host cell growth (e.g., as a readout of interaction of two molecules (e.g., proteins or protein fragments), other methods may be utilized for identifying and/or characterizing interaction including, but not limited to, cell-free assays, fluorescence resonance energy transfer (FRET), and other methods well known in the art.

Cell-free assays involve preparing a reaction mixture of the target gene protein and the test compound under conditions and for a time sufficient to allow the two components to interact and bind, thus forming a complex that can be removed and/or detected.

The interaction between two molecules (e.g., a first and a second polypeptide sequence) can also be detected and/or characterized using fluorescence energy transfer (FRET) (See, e.g., Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorometer).

In another embodiment, characterizing the ability of a first polypeptide sequence to bind to a second polypeptide sequence can be accomplished using real-time Biomolecular Interaction Analysis (BIA) (See, e.g., Sjolander and Urbaniczky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIA-CORE). Changes in the mass at the binding surface (e.g., indicative of a binding event) result in alterations of the refractive index of light near the surface (the optical phenomenon of surface plasmon resonance (SPR)), resulting in a detectable signal that can be used as an indication of real-time reactions between biological molecules.

Test compounds can be applied to host cells (e.g., in vivo or in vitro) at varying dosages, and the response of these cells monitored (e.g., for growth over various time periods). Physical characteristics of these cells can be analyzed by observing cells by microscopy. The induction of expression of new or increased levels of proteins such as enzymes, receptors and other cell surface molecules can be analyzed with any technique known in the art. Thus, host cells of the present invention can be used to determine the effect of test compounds (e.g., small molecule inhibitors, pharmaceuticals, biological agents, etc.) on polypeptide-polypeptide (e.g., protein-protein) interaction.

The ability of test compounds to alter (e.g., increase or decrease) specific protein interaction, while concurrently not altering other protein interaction can also be assayed using the compositions and methods of the present invention. For example, in some embodiments, two or more separate combinations of protein-protein interactors can be assayed in the same cell. For example, a host cell may comprise a first nucleic acid sequence and a second nucleic acid sequence, the first nucleic acid sequence encoding a polypeptide sequence comprising a first and second region, the first region comprising a Tat signal sequence and the second region comprising a bait polypeptide, and the second nucleic acid sequence encoding a second polypeptide sequence comprising a first and second region, the first region comprising a marker protein and the second region comprising a prey peptide, wherein the bait and prey peptides are known to interact, and a third nucleic acid sequence and a fourth nucleic acid sequence, the third nucleic acid sequence encoding a polypeptide sequence comprising a first and second region, the first region comprising a Tat signal sequence and the second region comprising a bait polypeptide, and the fourth nucleic acid sequence encoding a polypeptide sequence comprising a first and second region, the first region comprising a marker protein and the second region comprising a prey peptide, wherein the bait and prey polypeptide sequences are also known to interact with each other, wherein the marker protein of the second nucleic acid sequence and the fourth nucleic acid sequence are different (e.g., such that if interaction is altered (e.g., inhibited) between one of the interacting pairs of polypeptides but not the other, growth of the host cell will be altered when exposed to certain types of selective pressure (e.g., antibiotic) but not to other types of selective pressure (e.g., antibiotic). Screening in this way permits the identification of compounds that can be utilized (e.g., independently, in a pharmaceutical composition, or co-administered) for altering (e.g., enhancing or inhibiting) specific protein interactions while having no harmful effect (e.g., altering interaction) of other interactions.

In some embodiments, test compounds can be solubilized and added to host cells (e.g., in vitro (e.g., in the culture medium), or, in vivo (e.g., to a recipient subject that has received a host cell graft). In some embodiments, various concentrations of the test compound are utilized to determine an efficacious dose. In some embodiments, administration of the test compound is consistent over a period of time (e.g., administered one, two or more times a day) so as to keep the concentration of the test compound constant.

Test compounds can be administered in vitro or in vivo at a variety of concentrations. For example, in some embodiments, test compounds are added to culture medium or to a subject so as to achieve a concentration from about 10 pg/ml to 10 mg/ml, or from about 1 ng/ml (or 1 ng/cc of blood) to 100 ng/ml (or 100 ng/cc of blood), although higher (e.g., greater than 10 mg/ml) and lower (e.g., less than 10 pg/ml) concentrations may also be used.

The effects of a test compound can also be identified on the basis of a significant difference relative to a control regarding criteria such as the ratios of cell viability, proliferation rate, number of host cells, host cell alterations in gene expression and expressed phenotypes.

It is contemplated that a successfully identified test compound (e.g., a test compound, analogue or mimetic identified that is capable of altering (e.g., enhancing or inhibiting) protein interactions can be utilized in a pharmaceutical composition (e.g., to be administered to a subject (e.g., systemically or locally) to alter the protein interaction in the subject (e.g., thereby generating a desired result (e.g., inhibition of receptor stimulation in a cancer patient) in a subject. Thus, the compositions can also be prepared as injectables, either as liquid solutions or suspensions; solid forms suitable for solution in, or suspension in, liquid prior to injection may also be prepared. The compositions of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

It may be desirable to administer an analogue of a successfully identified test compound. A variety of designs for such mimetics are possible. For example, cyclic peptides, in which the necessary conformation for binding is stabilized by non-peptides, are specifically contemplated. (See, e.g., U.S. Pat. No. 5,192,746 to Lobl et al., U.S. Pat. No. 5,169,862 to Burke, Jr. et al., U.S. Pat. No. 5,539,085 to Bischoff et al., U.S. Pat. No. 5,576,423 to Aversa et al., U.S. Pat. No. 5,051,448 to Shashoua, and U.S. Pat. No. 5,559,103 to Gaeta et al., all hereby incorporated by reference, describe multiple methods for creating such compounds).

Synthesis of nonpeptide compounds that mimic peptide sequences is also known in the art. For example, Eldred et al., J. Med. Chem. 37:3882 (1994), describe nonpeptide antagonists that mimic the Arg-Gly-Asp sequence. Likewise, Ku et al., J. Med. Chem. 38:9 (1995) give further elucidation of the synthesis of a series of such compounds. Such nonpeptide compounds are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexyl-carbodiimide (DCC). The attack of a free amino group on the activated carboxyl leads to the formation of a peptide bond and the release of dicyclohexylurea. It may be important to protect potentially reactive groups other than the amino and carboxyl groups intended to react (e.g., the x-amino group of the component containing the activated carboxyl group can be blocked with a tertbutyloxycarbonyl group). This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

The methods of the present invention can be practiced in vitro, ex vivo, or in vivo.

In many drug screening programs that test libraries of compounds and natural extracts, high throughput assays are desirable in order to maximize the number of compounds surveyed in a given period of time. Screening assays of the present invention can be carried out in such a format, and accordingly may be used as a "primary" screen. Accordingly, in some embodiments, the present invention provides a protein-protein interaction assay comprising specific bait and prey fusion proteins known to interact, and a test compound of interest. In some embodiments, detection and quantification of host cell growth (e.g., under selective (e.g., antibiotic) pressure) provides a means for determining a test compound's efficacy at altering (e.g., inhibiting or potentiating) interaction between the bait and prey polypeptides. In some embodiments, the approximate efficacy of the test compound can be determined by generating dose response curves from host cell growth data obtained using various concentrations of the test compound. Moreover, in some embodiments, a control assay is performed to provide a baseline for comparison. In the control assay, host cell growth is quantitated in the absence of the test compound.

In some embodiments, nucleic acid sequences encoding bait and/or prey fusion protein that form a bait-prey complex are expressed in the same cell with a peptide library with the goal of identifying peptides that alter (e.g., potentiate or inhibit) the bait-prey interaction. Many techniques are known in the art for expressing peptide libraries intracellularly. In one embodiment, the peptide library is provided as part of a chimeric thioredoxin protein (e.g., expressed as part of the active loop).

In yet another embodiment, compositions and methods of the invention can be generated in the form of a diagnostic assay to detect the interaction of two proteins (e.g., where the gene from one protein is isolated from a biopsied cell). For example, there are many situations where it is desirable to detect mutants that, while expressed at appreciable levels in the cell, are defective at binding other cellular proteins. Such mutants may arise, for example, from fine mutations (e.g., point mutants) that may be impractical to detect by diagnostic DNA sequencing techniques or by immunoassays. Thus, in some embodiments, the present invention provides diagnostic screening assays that generally comprise cloning one or more cDNAs from a sample of cells, and expressing the cloned gene(s) in host cells under conditions that permit detection of an interaction between the recombinant gene product and a bait and/or prey protein. Accordingly, in some embodiments, the present invention provides a convenient method for identifying and/or characterizing mutations in genes encoding proteins that are unable to physically interact with a protein via detecting growth of host cells in a bait/prey-dependent fashion as described above.

In some embodiments, compositions and methods of the invention can be used to identify or optimize DNA-protein interactions. For example, compositions and methods of the present invention can be used to identify mutant or composite DNA binding domains having desired sequence binding preferences. The present invention can also be used to identify DNA sequences that are selectively bound by a given DNA binding protein and/or to determine the sequence specificity of a DNA binding protein.

In some embodiments, the present invention provides a method of detecting protein-RNA interactions (See, e.g., U.S. Pat. No. 5,750,667, hereby incorporated by reference in its entirety).

In some embodiments, compositions and methods of the present invention may be included in a kit for detecting an interaction between two proteins. In some embodiments, a kit for detecting a protein-protein interaction includes two vectors and a host cell. In some embodiments, a kit comprises a cell comprising a first nucleic acid encoding a fusion protein and a second nucleic acid encoding a second fusion protein, the first fusion protein comprising a Tat signal sequence and a first test polypeptide, the second fusion protein comprising a marker protein and a second test polypeptide.

The present invention contemplates the use of any protein of interest as a test polypeptide (e.g., bait and/or prey polypeptide). Thus, the bait and/or prey polypeptide may be any protein of interest or portion thereof to which another polypeptide (e.g., bait and/or prey polypeptide) may bind. For example, the bait and/or prey polypeptide may be Alzheimer's amyloid peptide (Aβ), SOD1, presenillin 1 and 2, renin, α-synuclein, amyloid A, amyloid P, activin, anti-HER-2, bombesin, enkephalinase, protease inhibitors, therapeutic enzymes, α1-antitrypsin, mammalian trypsin inhibitor, mammalian pancreatic trypsin inhibitor, calcitonin, cardiac hypertrophy factor, cardiotrophins (such as cardiotrophin-1), CD proteins (such as CD-3, CD-4, CD-8 and CD-19), CFTR, CTNF, DNase, human chorionic gonadotropin, mouse gonadotropin-associated peptide, cytokines, transthyretin, amylin, lipoproteins, lymphokines, lysozyme, a growth hormone (including human growth hormone), bovine growth hormone, growth hormone releasing factor, parathyroid hormone, thyroid stimulating hormone, growth factors, brain-derived neurotrophic growth factor, epidermal growth factor (EGF), fibroblast growth factor (such as α FGF and β FGF), insulin-like growth factor-I and -II, des(1-3)-IGF-I (brain IGF-I), insulin-like growth factor binding proteins, nerve growth factor (such as NGF-β), platelet-derived growth factor (PDGF), vascular endothelial growth factor (VEGF), receptors for growth hormones or growth factors, transforming growth factor (TGF) (such as TGF-α, TGF-β1, TGF-β2, TGF-β3, TGF-β4 or TGF-β5), neurotrophic factors (such as neurotrophin-3, -4, -5, or -6), gelsolin, glucagon, kallikreins, mullerian-inhibiting substance, neurotrophic factors, p53, protein A or D, prorelaxin, relaxin A-chain, relaxin B-chain, rheumatoid factors, rhodopsin, a serum albumin (such as human serum albumin), inhibin, insulin, insulin chains, insulin A-chain, insulin β-chain, insulin receptor, proinsulin, luteinizing hormone, integrin, interleukins (ILs) (such as IL-1 to IL-10, IL12, IL-13), erythropoietin, thrombopoietin, fibrillin, follicle stimulating hormone, clotting factors (such as factor VIIIC, factor IX, tissue factor, and von Willebrands factor, anti-clotting factors (such as Protein C, atrial naturietic factor, lung surfactant), a plasminogen activator (such as human tissue plasminogen activator or urokinase), thrombin, tumor necrosis factor-α or β, α-ketoacid dehydrogenase, addressins, bone morphogenetic proteins (BMPs), collagen, colony stimulating factors (CSFs) (such as M-CSF, GM-CSF and G-CSF), decay accelerating factor, homing receptors, interferons (such as interferon-α, -β and -γ), keratin, osteoinductive factors, PRNP, regulatory proteins, superoxide dismutase, surface membrane proteins, transport proteins, T-cell receptors, viral antigens such as a portion of the AIDS envelope, immunoglobulin light chain, antibodies, antibody fragments (such as single-chain Fv fragment (scFv), single-chain antibody (scAb), $F_{AB}$ antibody fragment, diabody, triabody, fluorobody), antigens such as gp120(IIIb) immunotoxins, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, gp120, p300, CREB, AP1, ras, NFAT, jun, fos, dentaorubral pallidoluysian atrophy-associated protein, a microbial protein (e.g., maltose binding protein, ABC transporter, glutathione S transferase, thioredoxin, β-lactamase), green fluorescent protein, red fluorescent protein, or derivatives or active fragments or genetic variants of any of the peptides listed above. The polypeptides may be native or mutated polypeptides, and preferred sources for such mammalian polypeptides include, but are not limited to, human, bovine, equine, porcine, lupine and rodent sources, with human proteins being particularly preferred.

In some embodiments, the marker protein is all or a portion of a drug resistant marker (e.g., an antibiotic resistance protein). In some embodiments, the antibiotic resistant protein is encoded by all or a portion of the aada gene, the streptomycin phosphotransferase (SPT) gene, the neomycin phosphotransferase gene (NPTII), the hygromycin phosphotransferase (HPT) gene, or genes encoding resistance to ampicillin, tetracycline, or chloramphenicol. In some embodiments, the marker protein is an enzyme or a portion of an enzyme that can be readily assayed (such as alkaline phosphatase, β-galactosidase, β-glucoronidase, chloramphenicol acetyl transferase (CAT), DHFR, luciferase). In some embodiments, the marker protein is a fluorescent protein (such as green fluorescent protein (GFP), GFP-SsrA (See, e.g., DeLisa et al., 2002), yellow fluorescent protein (YFP), cyan fluorescent protein (CFP), blue fluorescent protein (BFP), red fluorescent protein (DsRed, mRFP) and genetic variants thereof).

Fusion protein nucleic acids of the present invention may comprise additional sequences, such as coding sequences within the same transcription unit, controlling elements such as ribosome binding sites, and polyadenylation sites, additional transcription units under control of the same or a different promoter, sequences that permit cloning, expression, and transformation of a host cell, and any such construct as may be desirable to provide in embodiments of the invention.

The fusion protein nucleic acids may also include a polynucleotide sequence that encodes a molecular tag that can facilitate separation of a host cell that expresses the fusion protein from a host cell that does not express the fusion protein. For example, an epitope for an antibody can function as a molecular tag; cells that express the fusion protein can then be immobilized by contacting the cells with a solid support to which is attached antibodies that specifically recognize the epitope. Other suitable molecular tags are well known to those of skill in the art, and include, for example, a poly-histidine tag, or a FLAG peptide.

For example, in some embodiments, the fusion protein construct may comprise a nucleic acid sequence encoding a FLASH binding motif. The use of a FLASH tag permits a greater range (e.g., nearly unlimited range) of potential attachment sites to a target protein (e.g., on the N-terminus, C-terminus or even embedded within the target protein—e.g., when C-terminal and/or N-terminal regions are being analyzed for the ability to interact with other proteins that may alter target protein solubility—e.g., chaperone proteins). The use of such tags enables one to identify a target protein from other proteins within a host cell.

The polynucleotides and sequences embodied in this invention can be obtained using, among other methods, chemical synthesis, recombinant cloning methods, PCR, or any combination thereof. PCR technology is the subject matter of U.S. Pat. Nos. 4,683,195; 4,800,159; 4,754,065; and 4,683,202 and described in PCR: THE POLYMERASE CHAIN REACTION (Mullis et al. eds, Birkhauser Press, Boston (1994)) and references cited therein. Alternatively, one of skill in the art can use the sequences provided herein, or available from other sources (e.g., www.ncbi.nlm.nih.gov) and a commercial DNA synthesizer, PCR, or other molecular biological techniques to synthesize or otherwise attain the nucleic acid sequence (e.g., DNA sequence) of any target protein of interest.

Once the target protein of interest, marker protein and Tat signal peptide are chosen, they may be operatively expressed in a recombinant vector. The vector may be expressed in vitro or in vivo for analyzing and/or altering target protein solubility and/or folding. As used herein, the term "vector" is used in reference to nucleic acid molecules that transfer nucleic acid (e.g., DNA) segment(s) from one cell to another. The term "vehicle" is sometimes used interchangeably with "vector." A nucleic acid sequence can be "exogenous" or "heterologous," which means that it is foreign to the cell into which the vector is being introduced or that the sequence is homologous to a sequence in the cell but in a position within the host cell nucleic acid in which the sequence is ordinarily not found. Vectors include, but are not limited to, plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1994, both incorporated herein by reference.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In addition to control sequences that govern transcription and translation, vectors and expression vectors may contain nucleic acid sequences that serve other functions as well, including, but not limited to, promoters and enhancers, multiple cloning sites, splicing sites, polyadenylation signals, origins of replication, selectable and screenable markers (e.g., described in U.S. patent application Ser. No. 11/194,635, hereby incorporated by reference in its entirety).

In some embodiments, in addition to the portion of the fusion protein, and nucleic acid sequences encoding the same, that contains a marker protein, a cell that contains a fusion protein nucleic acid construct of the present invention may be identified in vitro or in vivo by including a marker (e.g., either the same or different marker than that present in the fusion protein) in the expression vector. Such markers confer an identifiable change to the cell permitting easy identification of cells containing the expression vector. Generally, a selectable marker is one that confers a property that allows for selection. A positive selectable marker is one in that the presence of the marker allows for its selection, while a negative selectable marker is one in which its presence prevents its selection. An example of a positive selectable marker is a drug resistance marker.

The inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a protein of the present invention. Further examples of selectable and screenable markers are well known to one of skill in the art.

With regard to the expression of fusion proteins of the present invention, once a suitable fusion protein nucleic acid encoding sequence has been obtained, one may proceed to prepare an expression system (e.g., expressing fusion protein constructs within host cells). The engineering of DNA segment(s) for expression in a prokaryotic or eukaryotic system may be performed by techniques generally known to those of skill in recombinant expression.

It is believed that virtually any expression system may be employed in the expression of the proteins of the present invention. Prokaryote- and/or eukaryote-based systems can be employed for use with the present invention to produce nucleic acid sequences, or their cognate polypeptides, proteins and peptides. Many such systems are commercially and widely available.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

It is contemplated that bait and prey polypeptides of the present invention may be co-expressed with other selected proteins, polypeptides or peptides (e.g., test compounds, protein chaperones, binding partners, and the like, or mutant forms thereof), wherein the proteins are co-expressed in the same cell or gene(s) may be provided to a cell that already has bait and/or prey polypeptides. Co-expression may be achieved by co-transfecting the cell with multiple distinct recombinant vectors, each bearing a copy of the respective DNA. Alternatively, a single recombinant vector may be constructed to include the coding regions for each of the bait and prey polypeptides and/or test compound of interest and/or a co-expressed protein or portion thereof (e.g., a chaperone) that can then be expressed in cells transfected with the single vector. In either event, the term "co-expression" herein refers to the expression of both at least one selected nucleic acid encoding one or more polypeptides (e.g., bait and/or prey polypeptides) and at least a second selected nucleic acid or gene encoding at least one or more secondary polypeptides (e.g., test compound) in the same recombinant cell.

It is contemplated that proteins may be expressed in cell systems or grown in media that enhance protein production. One such system is described in U.S. Pat. No. 5,834,249, incorporated herein by reference in its entirety. In some embodiments, a fusion protein may be co-expressed with one or more proteins that enhance refolding. Such proteins that enhance refolding include, for example, DsbA or DsbC proteins. A cell system co-expressing the DsbA or DsbC proteins are described in U.S. Pat. No. 5,639,635, incorporated herein by reference in its entirety. In certain embodiments, it is contemplated that a temperature sensitive expression vector may be used to aid assaying protein folding (e.g., at lower or higher temperatures than many $E.$ $coli$ cell strain's optimum growth at about 37° C.). For example, temperature sensitive expression vectors and host cells that express proteins at or below 20° C. are described in U.S. Pat. Nos. 5,654,169 and 5,726,039, each incorporated herein by reference in their entireties.

As used herein, the terms "engineered" and "recombinant" cells or host cells are intended to refer to a cell into which an exogenous DNA segment or gene, such as a cDNA or gene encoding at least one test polypeptide has been introduced. Therefore, engineered cells are distinguishable from naturally occurring cells that do not contain a recombinantly introduced exogenous DNA segment or gene. Engineered cells are thus cells having a gene or genes introduced through human intervention. Recombinant cells include those having an introduced cDNA or genomic gene, and also include genes positioned adjacent to a promoter not naturally associated with the particular introduced gene.

The present invention is not limited by the type of host cell. In some embodiments, prokaryotic host cells are $E.$ $coli$ K12 and its derivatives, $E.$ $coli$ B and its derivatives, $E.$ $coli$ MG1655 and its derivatives, $E.$ $coli$ X 1776 or W3110 (e.g., F-, λ-, or prototrophic,) $E.$ $coli$ MC4100 derivatives such as B0D, B1LK0, DADE, JARV16, $E.$ $coli$ LE392, and RR1; bacilli such as $Bacillus$ $subtilis$; and other enterobacteriaceae such as $Salmonella$ $typhimurium,$ $Serratia$ $marcescens,$ and various $Pseudomonas$ species. However, potential host cells are not limited to these examples. Indeed, a host cell may be any species of bacteria selected from the group consisting of $Acetobacter,$ $Actinomyces,$ $Aerobacter,$ $Agribacterium,$ $Azotobacter,$ $Bacillus,$ $Bacteroides,$ $Bordetella,$ $Brucella,$ $Chlamydia,$ $Clostridium,$ $Corynebacterium,$ $Erysipelothrix,$ $Escherichia,$ $Francisella,$ $Fusobacterium,$ $Haemophilus,$ $Klebsiella,$ $Lactobacillus,$ $Listeria,$ $Mycobacterium,$ $Myxococcus,$ $Neisseria,$ $Nocardia,$ $Pasteurella,$ $Proteus,$ $Pseudomonas,$ $Rhizobium,$ $Rickettsia,$ $Salmonella,$ $Serratia,$ $Shigella,$ $Spirilla,$ $Spirillum,$ $Staphylococcus,$ $Streptococcus,$ $Streptomyces,$ $Trepanema,$ $Vibrio,$ and $Yersinia$ (e.g., that comprise components useful in assays of the present invention).

In general, plasmid vectors containing replicon and control sequences which are derived from species compatible with the host cell are used in connection with the appropriate hosts. The vector ordinarily carries a replication site, as well as marking sequences that are capable of providing phenotypic selection in transformed cells. For example, $E.$ $coli$ is often transformed using derivatives of pBR322, a plasmid derived from an $E.$ $coli$ species. pBR322 contains genes for ampicillin and tetracycline resistance and thus provides easy means for identifying transformed cells. The pBR plasmid, or other microbial plasmid or phage may also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage λ GEM$^{TM-11}$ may be utilized in making a recombinant phage vector which can be used to transform host cells, (e.g., $E.$ $coli$ LE392).

Other useful vectors include pIN vectors (See, e.g., Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

In preferred embodiments, recombinant fusion proteins (e.g., Tat signal sequence-test polypeptide) of the present invention are expressed in prokaryotic host cells.

While it is conceivable that a fusion protein may be delivered directly, a preferred embodiment involves providing a nucleic acid encoding a fusion protein of the present invention to a cell. Following this provision, the fusion protein is synthesized by the transcriptional and translational machinery of the cell. In some embodiments, additional components useful for transcription or translation may be provided by the expression construct comprising fusion protein nucleic acid sequence.

In some embodiments, the nucleic acid encoding a fusion protein (e.g., Tat signal sequence-bait polypeptide) may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on, among other things, the type of expression construct employed.

The ability of certain viruses to infect cells or enter cells via receptor-mediated endocytosis, and to integrate into host cell genome and express viral genes stably and efficiently have made them attractive candidates for the transfer of foreign genes into mammalian cells. In some embodiments, vectors of the present invention are viral vectors (e.g., phage or adenovirus vectors).

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (See, e.g., Ghosh and Bachhawat, 1991, Targeted Diagn Ther. 4:87-103). Also contemplated is an expression construct complexed with LIPOFECTAMINE (Gibco BRL).

Liposome-mediated nucleic acid delivery and expression of foreign DNA in vitro has been very successful (See, e.g., Nicolau and Sene, 1982; Biochim Biophys Acta.; 721(2): 185-90). Wong et al. (Gene. 1980; 10(2):87-94) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (See, e.g., Kaneda et al., 1989 J Biol Chem.; 264(21):12126-9). In other embodiments, the liposome may be complexed or employed in conjunction with nuclear non-histone chromosomal proteins (HMG-1) (See, e.g., Kato et al., 1991, J Biol Chem. 1991; 266(6):3361-4). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

In certain embodiments of the present invention, the expression construct is introduced into the cell via electroporation. Electroporation involves the exposure of a suspension of cells (e.g., bacterial cells such as *E. coli*) and DNA to a high-voltage electric discharge.

Transfection of eukaryotic cells using electroporation has been quite successful. Mouse pre-B lymphocytes have been transfected with human kappa-immunoglobulin genes (See, e.g., Potter et al., 1984, Proc Natl Acad Sci USA.; 81(22): 7161-5), and rat hepatocytes have been transfected with the chloramphenicol acetyltransferase gene (See, e.g., Tur-Kaspa et al., 1986, Proc Natl Acad Sci USA.; 83(6):1627-31) in this manner.

In other embodiments of the present invention, the expression construct is introduced to the cells using calcium phosphate precipitation. Human I<B cells have been transfected with adenovirus 5 DNA (Graham and Van Der Eb, 1973) using this technique. Also in this manner, mouse L (A9), mouse C127, CHO, CV-1, BHK, NIH3T3 and HeLa cells have been transfected with a neomycin marker gene (See, e.g., Chen and Okayama, 1987, Mol Cell Biol.; 7(8):2745-52.), and rat hepatocytes were transfected with a variety of marker genes (See, e.g., Rippe et al., 1990, Mol Cell Biol.; 10(2):689-95).

In another embodiment, the expression construct is delivered into the cell using DEAE-dextran followed by polyethylene glycol.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force. The microprojectiles used have utilized biologically inert substances such as tungsten or gold beads.

Further embodiments of the present invention include the introduction of the expression construct by direct microinjection or sonication loading. Direct microinjection has been used to introduce nucleic acid constructs into *Xenopus* oocytes (See, e.g., Harland and Weintraub, 1985, J Cell Biol.; 101(3):1094-9), and LTK⁻ fibroblasts have been transfected with the thymidine kinase gene by sonication loading (See, e.g., Fechheimer et al., 1987, Proc Natl Acad Sci USA.; 84(23):8463-7).

In certain embodiments of the present invention, the expression construct is introduced into the cell using adenovirus assisted transfection. Increased transfection efficiencies have been reported in cell systems using adenovirus coupled systems (See, e.g., Kelleher and Vos, 1994; Biotechniques; 17(6):1110-7).

Still further expression constructs that may be employed to deliver nucleic acid construct to target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention.

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (See, e.g., Wu and Wu, 1987, Nucleic Acids Res.; 15(15):5913-23).

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding.

Homologous recombination (See, e.g., Koller and Smithies, 1992 Annu Rev Immunol.; 10:705-30) allows the precise modification of existing genes, overcomes the problems of positional effects and insertional inactivation, and allows the inactivation of specific genes, as well as the replacement of one gene for another. Methods for homologous recombination are described in U.S. Pat. No. 5,614,396, incorporated herein in its entirety by reference.

Thus, in some embodiments, the delivery of constructs (e.g., comprising nucleic acid encoding a fusion protein of the present invention) involves the use of homologous recombination. Homologous recombination relies, like antisense, on the tendency of nucleic acids to base pair with complementary sequences. The base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used generally as follows. First, a site for integration is selected within the host cell. Sequences homologous to the integration site are then included in a genetic construct, flanking the selected gene to be integrated into the genome. Flanking, in this context, simply means that target homologous sequences are located both upstream (5') and downstream (3') of the selected gene. These sequences should correspond to some sequences upstream and downstream of the target gene. The construct is then introduced into the cell, permitting recombination between the cellular sequences and the construct.

As a practical matter, the genetic construct will normally act as far more than a vehicle to insert the gene into the genome. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, this technique may be used to "knock-out" (delete) or interrupt a particular gene. Thus, another approach for altering or mutating a gene involves the use of homologous recombination, or "knock-out technology". This is accomplished by including a mutated or vastly deleted form of the heterologous gene between the flanking regions within the construct. In some embodiments, the arrangement of a construct to effect homologous recombination might be as follows:

Vector 5'-flanking sequence . . . Tat signal peptide . . . bait polypeptide . . . flanking sequence-3'vector.

Thus, using this kind of construct, it is possible, in a single recombinatorial event, to (i) "knock out" an endogenous gene, (ii) provide a selectable marker for identifying such an event and (iii) introduce a transgene (e.g., nucleic acid encoding a bait protein of the present invention) for expression.

Another refinement of the homologous recombination approach involves the use of a "negative" selectable marker. One example is the use of the cytosine deaminase gene in a negative selection method as described in U.S. Pat. No. 5,624,830. The negative selection marker, unlike the selectable marker, causes death of cells that express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

Compositions and methods of the present invention also find use in the discovery of drugs that modulate protein-protein interaction. For example, the search for pharmaceuticals has focused on the identification of compounds that inhibit cellular processes. However, the increasing prevalence of diseases associated with protein misfolding (e.g., including, but not limited to, Huntington's disease, Alzheimer's disease, Parkinson's disease, cystic fibrosis, amyotropic lateral sclerosis, Creutzfeld-Jacob disease, and some forms of diabetes and cancer) presents a new challenge for the pharmaceutical industry. Thus, the present invention provides compositions and methods for use in screening and assaying protein-protein interaction related to these, and other diseases. For example, using the compositions and methods of the present invention, small molecules or other types of agents (e.g., test compounds) may be identified that stabilize protein-protein interaction of a mutant protein involved in disease (e.g., p53). It will be apparent to those skilled in the art that this, and other, aspects of the present invention are easily amenable to a high-throughput procedure to rapidly screen a large number of alternative small molecules or agents (e.g., from a library of such materials). In some embodiments, these methods provide for the development of automated procedures for screening of the small molecules or agents. Thus, the present invention provides incredible savings in time and resources for analyzing protein-protein interaction and materials (e.g., small molecules or agents) useful for altering the same.

Additionally, the compositions and methods of the present invention may be used to identify small molecules or other types of agents (e.g., test compounds) that can be used to destabilize protein-protein interaction. In some embodiments, the present invention provides methods for identifying an antibiotic agent.

For example, in some embodiments, the growth of host cells comprising test proteins that interact and that are contacted with a candidate agent (e.g., a test compound) is compared to growth of host cells comprising test proteins that interact that is not contacted with the test compound. A decrease in growth of the host cells contacted with the test compound is indicative of a test compound that inhibits protein-protein interaction in the cell. In some embodiments, the growth of the host cells, whether or not a test compound (e.g., drug or antibiotic agent) is being tested, is under a selective pressure (e.g., exposed to a drug, antibiotic or other selective means).

Test compounds, as described herein, may be any agent that potentially inhibits or enhances protein-protein interactions, including, but not limited to, a drug, a pharmaceutical, or a small molecule. Using lead compounds to help develop improved compounds is know as "rational drug design" and includes not only comparisons with know inhibitors and enhancers of protein folding/solubility, but predictions relating to the structure of target molecules.

The goal of rational drug design is to produce structural analogs of biologically active agents (e.g., test compounds). By creating such analogs, it is possible to fashion drugs, that are more active or stable than the natural molecules, that have different susceptibility to alteration or that may affect the function of various other molecules. In one approach, it is possible to generate a three-dimensional structure for a target molecule, or a fragment thereof. This could be accomplished by X-ray crystallography, computer modeling or by a combination of both approaches.

It also is possible to use antibodies to ascertain the structure of a test compound (e.g., enhancer or inhibitor of protein-protein interaction). In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful test compounds. Screening of such libraries, including combinatorially generated libraries (e.g., peptide libraries), is a rapid and efficient way to screen large number of related (and unrelated) agents for activity. Combinatorial approaches also lend themselves to rapid evolution of potential drugs by the creation of second, third and fourth generation compounds modeled of active, but otherwise undesirable compounds.

Test compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the agents (e.g., test compounds) to be screened could also be derived or synthesized from chemical compositions or man-made compounds. Thus, it is understood that a test compound identified by the present invention may be any peptide, polypeptide, polynucleotide, small molecule inhibitors or any other chemicals or compounds (e.g., that may be designed through rational drug design starting from known inhibitors or enhancers).

Other potential agents include antisense molecules, ribozymes, and antibodies (including single chain antibody fragments). Such compounds are described in greater detail elsewhere in this document. For example, an antisense molecule that bound to a translational or transcriptional start site, or splice junctions, would be ideal candidate inhibitors.

In addition to the test compounds initially identified, other sterically similar compounds may be formulated to mimic the key portions of the structure of the modulators. Such agents (e.g., compounds), that may include peptidomimetics of peptide modulators, may be used in the same manner as the initial modulators.

The invention also provides gene delivery vehicles and expression vectors and host or genetically modified cells containing at least polynucleotides of the invention and/or a fusion protein of the invention.

The present invention also provides gene delivery vehicles suitable for delivery and/or expression of a polynucleotide sequence (e.g., a nucleic acid sequence encoding a fusion protein of the present invention) of the invention into cells (whether in vivo, ex vivo, or in vitro). A polynucleotide sequence of the invention can be contained within a cloning or expression vector. These vectors can in turn be manipulated to assume any of a number of forms that may, for example, facilitate delivery to and/or entry into a cell. Examples of suitable expression and delivery vehicles are provided elsewhere herein.

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. In some embodiments, a host cell is used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes. Prokaryotes include gram negative or gram positive bacterial cells. Numerous cell lines and cultures are available for use as a host cell, and they can be obtained through the American Type Culture Collection (ATCC), an organization that serves as an archive for living cultures and genetic materials (www.atcc.org). An appropriate host can be determined by one of skill in the art based on the vector nucleic acid sequence and the desired result. A plasmid or cosmid, for example, can be introduced into a prokaryote host cell for replication of many vectors. Bacterial cells used as host cells for expression vector replication and/or expression include, among those listed elsewhere herein, DH5α, JM109, and KC8, as well as a number of commercially available bacterial hosts such as SURE Competent Cells and SOLOPACK Gold Cells (Stratagene, La Jolla). Alternatively, bacterial cells such as *E. coli* LE392 can be used as host cells for phage viruses.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector and/or expression of nucleic acid sequences present within the vector. Also understood and known are techniques and conditions that allow large-scale production of vectors, as well as production of the nucleic acids encoded by vectors and their cognate polypeptides, proteins, or peptides.

The invention also provides a method for screening for mutations in a test polypeptide sequence that improve or inhibit protein-protein interaction. For example, cells comprising a fusion protein of the present invention can be treated with a mutagen, and those host cells that display an increase in growth (e.g., rate or abundance) in the presence of a selective marker (e.g., ampicillin) identified. A "mutagen" is intended to include, but not be limited to chemical mutagens such as ethyl methane sulphonate, N-methyl-N'-nitroso-guanidine and nitrous acid as well as physical agents such as ionizing radiation.

In an alternative embodiment, mutations can be introduced into a polynucleotide sequence encoding a bait and/or prey polypeptide. The altered polynucleotide is then tested to determine whether protein-protein interaction is changed (e.g., as monitored by growth in a selective environment, e.g., in the presence of ampicillin). Such mutations include, but are not limited to, mutations induced by a mutagen; site directed mutations that alter specific amino acid residues such as mutation of cysteine residues to eliminate disulfide bonds; deletions that remove sets of specific amino acids such as deletion of a continuous stretch of hydrophobic amino acids; and fusions of the bait and/or prey polypeptide to a second, particularly soluble polypeptide. In each case, the solubility of the bait and/or prey protein is assessed by determining growth of the host cells in a selective environment.

Where employed, mutagenesis can be accomplished by a variety of standard, mutagenic procedures. Mutation can involve modification of the nucleotide sequence of a single gene, blocks of genes or whole chromosome. Changes in single genes may be the consequence of point mutations that involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemicals such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods Various types of mutagenesis (e.g., random mutagenesis (e.g., insertional mutagenesis, chemical mutagenesis, radiation mutagenesis, in vitro scanning mutagenesis, random mutagenesis by fragmentation and reassembly) and site specific mutagenesis (e.g., directed evolution) are described in U.S. patent application Ser. No. 11/194,635, hereby incorporated by reference in its entirety.

EXPERIMENTAL

The following examples are provided in order to demonstrate and further illustrate certain preferred embodiments and aspects of the present invention and are not to be construed as limiting the scope thereof.

Example 1

Materials and Methods

Bacterial strains and plasmids. Wildtype *E. coli* strain MC4100 and a ΔtatC derivative of MC4100, strain B1 LK0 (See, e.g., Bogsch et al., (1998) J Biol Chem 273: 18003-18006), were used for all protein interaction assay experiments. Plasmids generated in this study were derivatives of pBAD18-Kan and pBAD33 (See, e.g., Guzman et al., (1995) J Bacteriol 177: 4121-4130 unless otherwise noted. For generation of bait constructs (e.g., See FIG. 1), DNA encoding the ssTorA signal peptide (See, e.g., DeLisa et al., (2002) J Biol Chem 277: 29825-29831 was cloned into pBAD18-Kan between the SacI and XbaI restriction sites, leaving several additional restriction sites (e.g., XbaI, SalI, BamHI and HindIII) immediately after the ssTorA sequence for facile insertion of any target DNA sequence (e.g., encoding a bait protein of interest). The resulting plasmid is named pBAD18-ss-TorA-X where X refers to the sequence (e.g., bait sequence) under study. For generation of prey plasmids (e.g., See FIG. 1), the DNA encoding the β-lactamase (Bla) gene was cloned between XbaI and HindIII of plasmid pBAD33, leaving available several 5' (upstream) restriction sites for making fusions between a protein of interest (e.g., a prey protein) and the Bla protein. The resulting bait plasmid is named pBAD33-Y-Bla where Y refers to the protein (e.g., prey protein) under study. All plasmids constructed during development of the present invention were confirmed by DNA sequencing.

Cell growth assays. Cells carrying a bait plasmid, a prey plasmid or the two plasmids together were grown overnight in LB medium containing kanamycin (Kan; 25 µg/mL) and chloramphenicol (Cm; 25 µg/mL). Screening of cells on solid agar plates was performed by spotting 5 µL of 10×-diluted overnight cells directly onto LB agar plates supplemented with Ampicillin (Amp) (100 µg/mL) or Kan/Cm (25 µg/mL each) and growing overnight at room temperature as previously documented (See, e.g., Fisher et al., (2006) Protein Sci 15: 449-458; Lutz et al., (2002) Protein Eng 15: 1025-1030). Screening of cells in liquid culture was performed by diluting overnight cells 100 fold into fresh LB plus 100 µg/mL Amp in 96-well plates as previously described (See, e.g., Fisher et al., (2006) Protein Sci 15: 449-458; Lutz et al., (2002) Protein Eng 15: 1025-1030). Cells were grown aerobically at 30° C. for 6 h and growth rates were calculated from the absorbance change at 600 nm using a plate reader. All growth rate data is the average of three cultures grown in parallel. Error is reported as plus or minus the standard deviation of these data.

Protein analysis. Subcellular fractionation was performed using an ice-cold osmotic shock procedure (See, e.g., DeLisa et al., (2003) Proc Natl Acad Sci USA 100: 6115-6120; Sargent et al., (1998) EMBO J 17: 3640-3650). Western blotting of these fractions was performed as described in DeLisa et al., (2003) Proc Natl Acad Sci USA 100: 6115-6120. The quality of all fractionations was determined by immunodetection of the cytoplasmic GroEL protein (See, e.g., DeLisa et al., (2003) Proc Natl Acad Sci USA 100: 6115-6120). Finally, osmotic shockate (i.e., periplasmic fraction) was assayed for β-lactamase activity based on nitrocefin hydrolysis in 96-well format as described (See, e.g., Galarneau et al., (2002) Nat Biotechnol 20: 619-622.

Example 2

A System for Identification and Characterization of Protein-Protein Interactions During development of the present invention, a TAT-mediated Recognition of Associating Proteins (TRAP) system was developed and characterized for the ability to detect and characterize protein-protein interactions in bacteria (e.g., in *Escherichia coli*) (See, e.g., FIG. 1). A general premise for the TRAP system is built upon the twin-arginine translocation (Tat) machinery's ability to transport heterodimeric complexes to the bacterial (e.g., *E. coli*) periplasm (See, e.g., Rodrigue et al., (1999) J Biol Chem 274: 13223-13228). In the engineered system, a Tat signal peptide (e.g., ssTorA) is fused to a protein (e.g., a bait protein) of interest. Although an understanding of the mechanism is not necessary to practice the present invention and the present invention is not limited to any particular mechanism of action, in some embodiments, if the protein (e.g., bait protein) interacts with a corresponding protein (e.g., a prey protein), a heterodimer is formed in the cytoplasm that bears an N-terminal Tat signal peptide and a C-terminal marker (e.g., β-lactamase (Bla)) moiety. Following transport of the heterodimer into the periplasm by the Tat system, a marker may provide resistance to a selective environment (e.g., Bla degrades β-lactam antibiotics such as ampicillin (Amp)) thereby conferring growth to cells cultured in the presence of the selective environment (e.g., an antibiotic (e.g., ampicillin)). Although an understanding of the mechanism is not necessary to practice the present invention and the present invention is not limited to any particular mechanism of action, in some embodiments, general proofreading of interacting proteins for correct "foldedness" is a built-in feature of the TRAP system as the Tat system has previously been shown to exert folding quality control on its substrates (See, e.g., DeLisa et al., (2003) Proc Natl Acad Sci USA 100: 6115-6120; Fisher et al., (2006) Protein Sci 15: 449-458).

Example 3

Identification and Characterization of Protein-Protein Interactions

Figure 2:
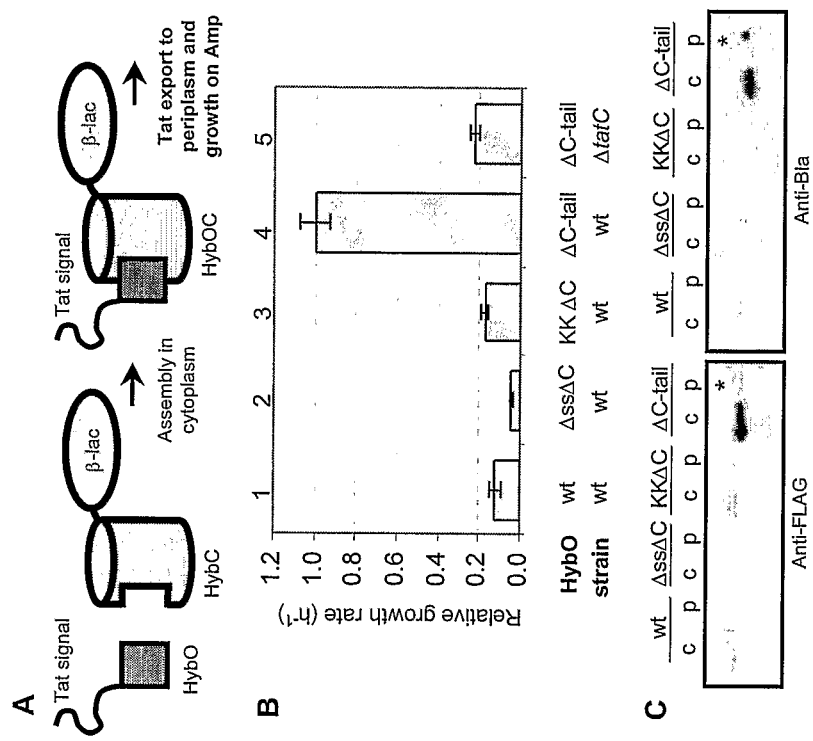
FIG. 2 shows (A) a bait-prey system comprising HybO and HybC generated during development of the present invention; (B) the ability of various HybO constructs to confer growth of *E. coli* cells on ampicillin (Amp) plates; and (C) Western blot analysis of cytoplasmic (c) and periplasmic (p) fractions of cells expressing bait and prey constructs.

In order to determine whether the Tat system could be used as a genetic selection for protein interactions, a bait-prey system was developed based on a naturally occurring Tat substrate complex shown to transit the inner membrane via a hitchhiker mechanism (See, e.g., Rodrigue et al., (1999) J Biol Chem 274: 13223-13228). Specifically, the *E. coli* hydrogenase-2 complex is comprised of two proteins, HybO and HybC. The HybO protein carries an N-terminal Tat signal peptide whereas the HybC protein carries no N-terminal signal peptide (See FIG. 2A). The two proteins are known to assemble into a heterodimer in the cytoplasm, prior to transport, and only after forming a stable dimeric complex are they delivered into the periplasm (See, e.g., Rodrigue et al., (1999) J Biol Chem 274: 13223-13228). A pBAD18-HybO plasmid along with a pBAD33-HybC-Bla plasmid were generated to determine if the interaction between HybO-HybC, where HybC was coupled to Bla, would confer growth to cells grown on Amp plates (See, e.g., FIG. 2A).

A wild-type HybO protein as bait did not confer growth to cells on Amp (See FIG. 2B, lane 1). It was suspected that this may have been due to the fact that following Tat transport the HybOC catalytic dimer is anchored at the periplasmic side of the cytoplasmic membrane by a single transmembrane segment located at the C-terminus of HybO (See, e.g., Hatzixanthis et al., (2003) Mol Microbiol 49: 1377-1390). Localization of HybOC in this fashion might be disruptive to Bla activity.

Indeed, when the C-terminal inner membrane anchoring motif was removed from HybO (ΔC-tail HybO), a deletion that is known to render the HybOC (the complex between HybO and HybC) soluble in the periplasm (See, e.g., Hatzixanthis et al., (2003) Mol Microbiol 49: 1377-1390), the HybO-HybC-Bla complex was able to confer growth to cells on Amp (See, e.g., FIG. 2B, lane 4). This was confirmed to be a Tat-specific phenomenon based on controls where: (a) the Tat targeting signal was entirely removed from ΔC-tail HybO (Δss ΔC, See FIG. 2B, lane 2); (b) the invariant twin arginine residues of the ΔC-tail HybO signal peptide were replaced with twin lysines (KK ΔC, See FIG. 2B, lane 3); or (c) the ΔC-tail HybO and HybC-Bla constructs were expressed in a ΔtatC mutant strain (See FIG. 2B, lane 5). Western blot analysis of the cytoplasmic (c) and periplasmic (p) fractions of cells expressing the above constructs was in complete agreement with liquid growth assays (See FIG. 2C), as the only bait protein that was able to localize the HybC-Bla prey to the periplasmic fraction was ΔC-tail HybO, indicated by asterisks. HybO constructs were detected using an anti-FLAG antibody specific for the C-terminal FLAG affinity tag appended to ΔC-tail HybO while HybC-Bla was detected using an anti-Bla antibody.

Example 4

Detection and Characterization of Interaction Between Eukaryotic Protein Interacting Domains (PIDs)

Figure 3:
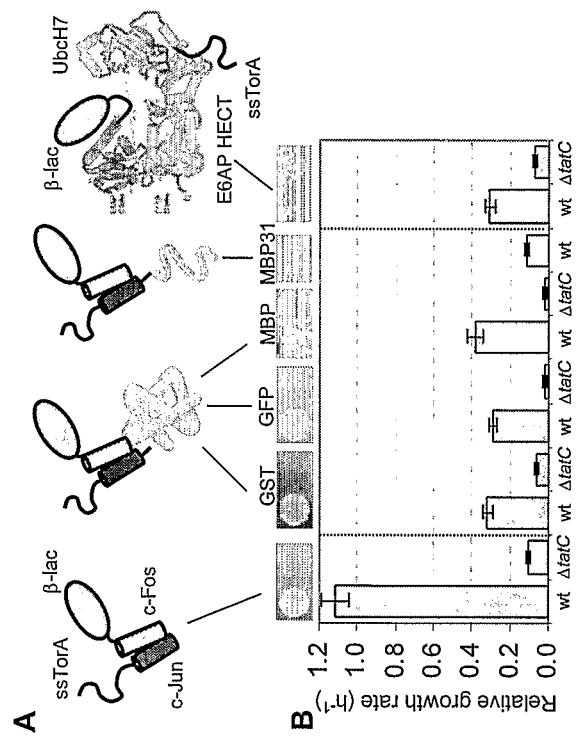
FIG. 3 shows (A) a bait-prey system comprising eukaryotic c-Jun and c-Fos generated during development of the present invention; and (B) the growth of *E. coli* cells comprising plasmids encoding various bait-prey combinations on ampicillin plates

To test the generality of the TRAP genetic selection system, a series of plasmids were generated for detecting interaction between eukaryotic protein domains known for their ability to interact with one another. First, a bait plasmid carrying the eukaryotic c-Jun leucine zipper motif (pBAD18-ssTorA-c-Jun) and a corresponding prey plasmid carrying the eukaryotic c-Fos leucine zipper motif (pBAD33-c-Fos-Bla) were co-expressed in wt *E. coli* cells and found to confer growth to cells grown on LB+Amp agar plates or in liquid LB supplemented with an equivalent amount of Amp (See FIG. 3, lane 1). The growth rate data in FIG. 3 is normalized to the growth observed for cells co-expressing ΔC-tail HybO and HybC-Bla. The fact that no growth was observed for ΔtatC cells expressing the same two constructs (See FIG. 3, lane 2) indicated that this was a Tat-specific phenomenon. Since c-Jun and c-Fos are relatively small protein domains, it was next determined whether inclusion of a larger protein moiety would inhibit the genetic selection strategy. To test this, glutathione-5-transferase (GST), green fluorescent protein (GFP) and maltose binding protein (MBP) were each fused to the C-terminus of c-Jun yielding ssTorA-c-Jun-GST, ssTorA-c-Jun-GFP; and ssTorA-c-Jun-MBP, respectively. These 3 proteins were chosen as all 3 had previously been found to transit the Tat system when each was engineered to carry the N-terminal ssTorA signal peptide (See, e.g., Fisher et al., (2006) Protein Sci 15: 449-458). Cells expressing bait c-Jun plasmids carrying these additional proteins were all found to grow on Amp (See FIG. 3, lanes 3, 5 and 7) indicating that the c-Jun-c-Fos interaction could still be detected even in the presence of other proteins (e.g., full length proteins (e.g., fused to the bait protein)). The level of growth was reduced (e.g., by about 70%) relative to the original c-Jun-c-Fos constructs, suggesting that these proteins may either interfere with the c-Jun-c-Fos interaction or reduce Tat transport efficiency of the heterodimer through the Tat system.

In order to determine if the Tat proofreading system was still active during transport of these engineered heterodimeric complexes, the MBP sequence in ssTorA-c-Jun-MBP was replaced with a variant of MBP (MBP31) that is known to misfold and be highly insoluble in the cytoplasm and, as a result, is prevented from transiting the inner membrane by the Tat system (See, e.g., Fisher et al., (2006) Protein Sci 15: 449-458). Consistent with these earlier studies, co-expression of the ssTorA-c-Jun-MBP31 construct with c-Fos-Bla did not confer growth to cells on Amp (See FIG. 3, lane 9).

In order to test the range of affinities that can be detected by the TRAP system, the eukaryotic UbCH7-E6AP (HECT) interacting pair having a much lower affinity (measured $K_D$=6 μm) (See, e.g., Eletr et al., (2005) Nat Struct Mol Biol 12: 933-934) than eukaryotic c-Jun-c-Fos (measured $K_D$=110 nm) (See, e.g., Pernelle et al., (1993) Biochemistry 32: 11682-11687) was tested. Wildtype cells, but not ΔtatC mutant cells, expressing ssTorA-UbCH7 from the bait plasmid and E6AP (HECT)-Bla from the prey plasmid were found to grow on LB+Amp plates and in liquid medium containing Amp (See FIG. 3, lanes 10 and 11). The level of growth was approximately 30% of that observed for the higher affinity interaction between c-Jun and c-Fos leucine zippers.

Example 5

Figure 4:
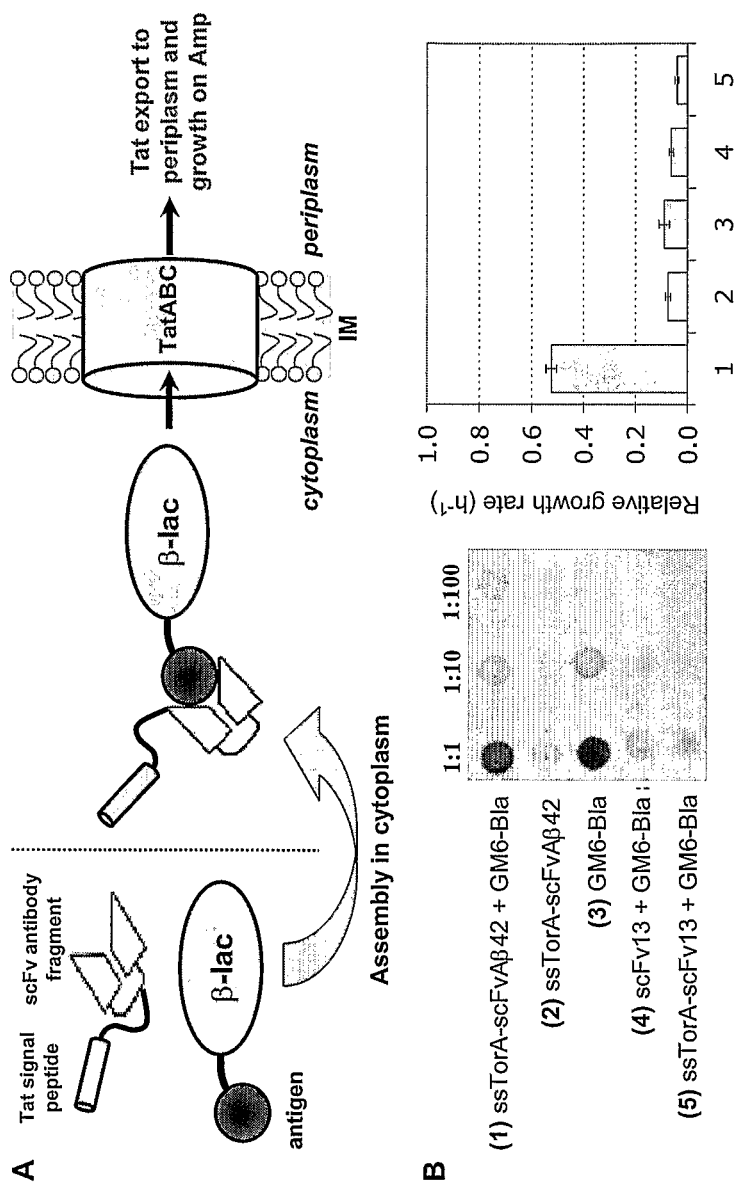
FIG. 4 shows (A) a bait-prey system comprising a single chain Fv antibody fragment and antigen; and (B) the growth of *E. coli* cells comprising plasmids encoding various bait-prey combinations on ampicillin plates

Use of the TRAP System for Engineering High-Affinity Intracellular Antibody Fragments To test the utility of the TRAP system for detecting the interaction between a single chain Fv antibody fragment (scFv) and its cognate antigen, plasmid pBAD18-ssTorA-scFvAβ42 was constructed. The scFvAβ42 sequence encodes an antibody fragment derived from spleen cells of mice immunized with human amyloid-beta 1-42 (Aβ42) peptide (See, e.g., Manoutcharian et al., (2003) J Neuroimmunol 145: 12-17). The prey in this experiment was a variant of the Aβ42 peptide, known as GM6, which is known to be highly soluble when expressed in the *E. coli* cytoplasm (See, e.g., Fisher et al., (2006) Protein Sci 15: 449-458; Wurth et al., (2002) J Mol Biol 319: 1279-1290). Upon co-expression of ssTorA-scFvAβ42 and GM6-Bla, cells were capable of growth on LB plates supplemented with Amp even when diluted 100× (See FIG. 4B). Liquid growth rate analysis (where the growth rate was normalized to that of cells expressing ΔC-tail HybO and HybC) indicated that cells expressing ssTorA-scFvAβ42 and GM6-Bla grew at a rate that was roughly 50% slower than the growth observed for cells expressing ΔC-tail HybO and HybC, but nearly 2× greater than what was observed for cells expressing the lower affinity UbCH7-E6AP (HECT) interacting domains. A number of controls indicated that the growth conferred by the ssTorA-scFvAβ42/GM6-Bla interaction was: (a) dependent on the association between the two constructs as expression of each construct alone did not confer growth (See FIGS. 4B, 2 and 3); (b) dependent on the specificity of Aβ42scFv for the GM6 antigen as a control scFv sequence (scFv13), which is known to be soluble in the cytoplasm but specific for a different antigen, was incapable of conferring growth when coexpressed with GM6-Bla (See FIG. 4B, 4); and (c) specific to the Tat system as no growth was observed when the ssTorAAβ42/GM6-Bla constructs were expressed in ΔtatC mutant cells or when the scFvAβ42 sequence was expressed without the ssTorA signal peptide (See FIG. 4B, 5).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method for screening for the ability of an intrabody and an antigen to interact comprising:
    a) introducing into a culture of bacterial host cells
        i) a plurality of first nucleic acid vectors encoding a combinatorial library of first fusion proteins comprising intrabody variants operably linked to a bacterial twin-arginine translocation (Tat) signal sequence so that said first fusion proteins are expressed in said bacterial host cells and
        ii) a second nucleic acid vector encoding a second fusion protein comprising an antibiotic resistance marker protein operably linked to said antigen so that said second fusion protein is expressed in said bacterial host cells;
    b) monitoring growth of the bacterial host cells under selective pressure by exposing the bacterial host cells to an antibiotic, wherein growth of a bacterial host cell in said culture is indicative of export of a heterodimeric complex of a first fusion protein comprising a Tat signal sequence operably linked to a selected variant of said intrabody and said second fusion protein; and
    c) identifying said selected variant of said intrabody.

2. The method of claim 1, wherein said antibiotic is ampicillin.

3. The method of claim 1, wherein said host cell is *E. coli*.

4. The method of claim 3, wherein said *E. coli* is *E. coli* strain MC4100.

5. The method of claim 1, wherein at least one of said first fusion proteins and said second fusion protein comprises a prokaryotic polypeptide sequence.

6. The method of claim 1, wherein the antigen comprises eukaryotic polypeptide sequences.

7. The method of claim 1, wherein said first fusion proteins are hormone receptor polypeptide sequences.

8. The method of claim 7, wherein said hormone receptor is a nuclear hormone receptor.

9. The method of claim 1, wherein said second fusion protein comprises a polypeptide sequence from a peptide library.

10. The method of claim 1, wherein said Tat signal sequence is ssTorA.

11. The method of claim 1, wherein said Tat signal sequence is selected from the group consisting of CueO, DmsA, FdnG, FdoG, HyaA, NapA, Sufi, WcaM, YagT, YcbK, YcdB, YdhX, and YnfE.

12. The method of claim 1, wherein said antibiotic resistance marker protein is β-lactamase.

13. The method of claim 1, wherein said antibiotic resistance marker protein is selected from the group consisting of a streptomycin phosphotransferase, a neomycin phosphotransferase, a hygromycin phosphotransferase, a protein encoded by the aada gene, a protein encoding resistance to ampicillin, a protein encoding resistance to tetracycline, a protein encoding resistance to chloramphenicol, alkaline phosphatase, β-galactosidase, β-glucuronidase and chloramphenicol acetyl transferase (CAT).

* * * * *